(12) United States Patent
Kukreja

(10) Patent No.: US 7,091,207 B2
(45) Date of Patent: Aug. 15, 2006

(54) METHOD OF TREATING MYOCARDIAL INFARCTION WITH PDE-5 INHIBITORS

(75) Inventor: Rakesh Kukreja, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 343 days.

(21) Appl. No.: 10/443,148

(22) Filed: May 22, 2003

(65) Prior Publication Data

US 2004/0009957 A1    Jan. 15, 2004

Related U.S. Application Data

(60) Provisional application No. 60/382,088, filed on May 22, 2002, provisional application No. 60/402,060, filed on Aug. 9, 2002.

(51) Int. Cl.
*A61K 31/519* (2006.01)
*A61K 31/535* (2006.01)
*A61K 31/497* (2006.01)

(52) U.S. Cl. .............. 514/258.1; 514/259.1; 514/234.5

(58) Field of Classification Search .......... 514/258.1, 514/262.1, 252.03, 312, 256, 287, 509, 252, 514/258, 267, 292, 303, 262.03, 259.1, 234.5, 514/252.16

See application file for complete search history.

(56) References Cited

U.S. PATENT DOCUMENTS 4,337,254 A * 6/1982 Moncada ............... 514/263.31

6,362,178 B1   3/2002 Niewohner et al.

FOREIGN PATENT DOCUMENTS

WO    WO 9920251 A1 *  4/1999

OTHER PUBLICATIONS

"The Role of cGMP Hydrolysing Phosphodiesterases 1 and 5 in Cerebral Artery Dilation", Kruuse et al., Eur J Pharmacol, abstract, May 18, 2001; 420(1):55-65.*
"Acute Myocardial Infarction Following Sildenafil Citrate (Viagra) intake in a Nitrate-Free Patient", Porter et al., abstract, Clin. Cardiol., 1999, Nov. 22(11):762-3.*
"Levitra: Treatment of Sexual Dysfunction", Patient Information Brochure, 2006, www.msabout.com.*
"CIALIS", Patient Information Brochure, www.cialis.com, 2005.*
"Viagra" Paitent Information Brochure, 2005, Pfizer Inc.*
Hefting et al. "Role of apoptosis in reperfusion injury" Cardiovascular Research; Feb. 15, 2004 pp. 414-426.
Das et al. "Cardioprotection with sildenafil, a selective inhibitor of cyclic 3', 5'-monophosphate specific phophodiesterase 5", Drugs under Expreimental and Clinical Research; 2002 pp. 213-219.
Ockaili et al. "Slidenafil (Viagra) Induces powerful cardioptotective effect via opening of mitochondrial KATP channels in rabbits" American Journal of Physiology (2002) pp. H1263-H1269.

* cited by examiner

*Primary Examiner*—Brian-Yong S. Kwon
(74) *Attorney, Agent, or Firm*—Whitham, Curtis, Christofferson & Cook, PC

(57) ABSTRACT

A method is provided for the prevention of ischemia/reperfusion injury, for example, in patients undergoing heart surgery, and involves the administration of a phosphodiesterase-5 (PDE-5) inhibitor such as sildenafil. The method may also be used during or after a heart attack to prevent or lessen ischemic heart damage.

9 Claims, 8 Drawing Sheets

Figure 1.
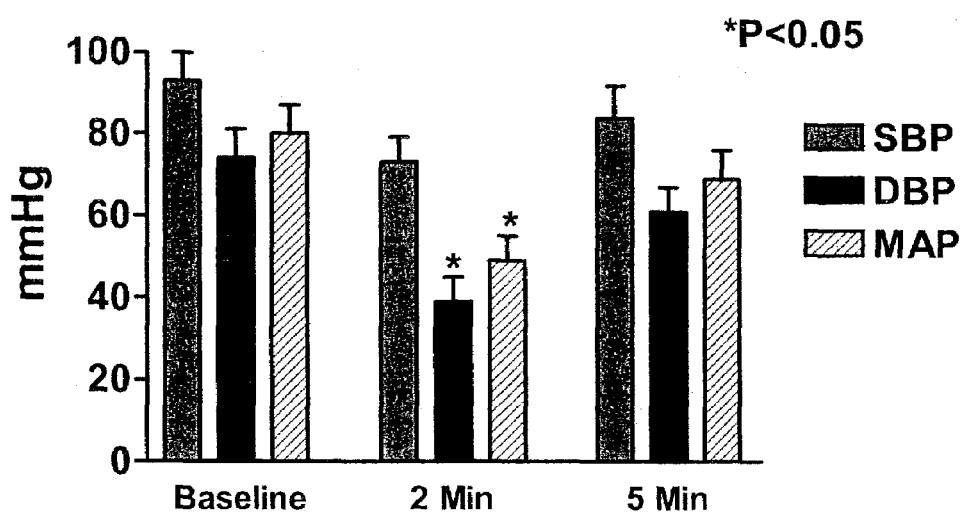
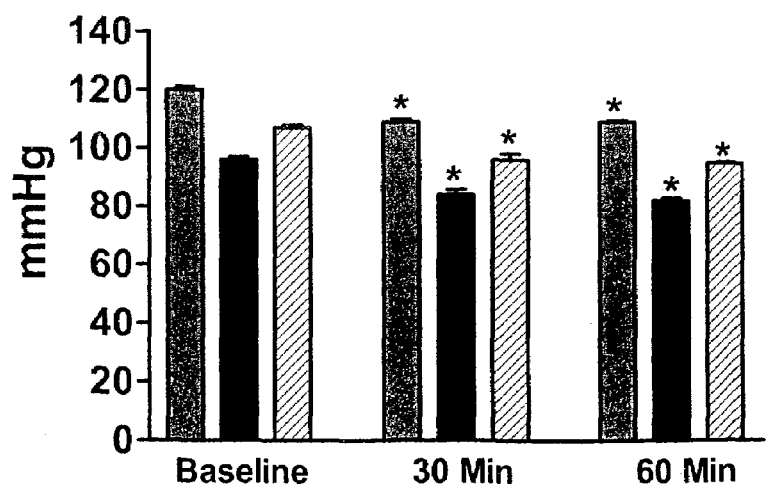

Figure 2
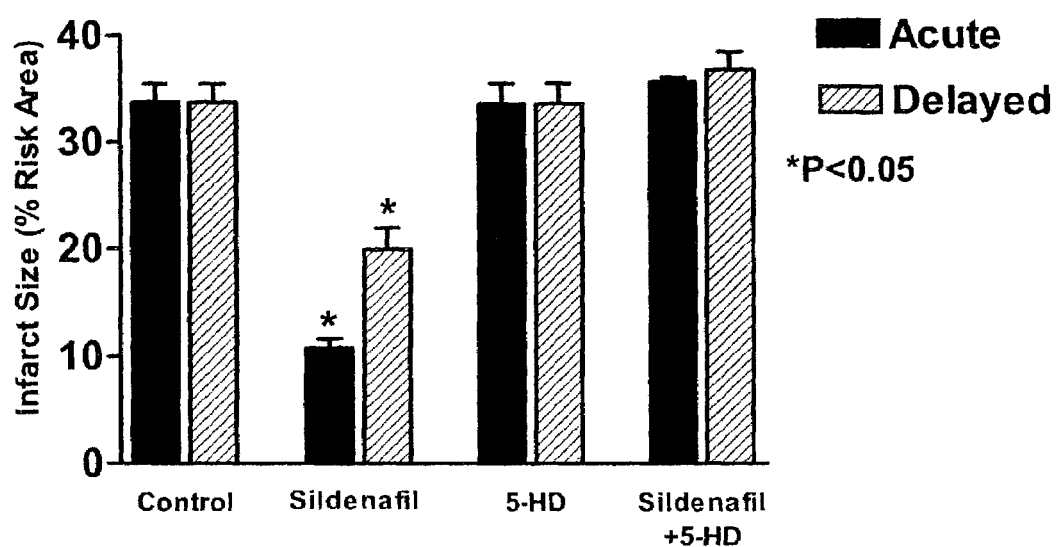
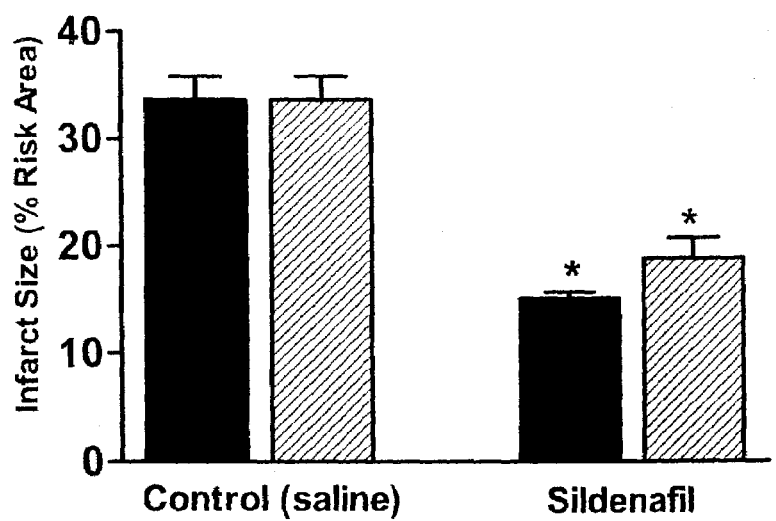

Figure 6A & B

METHOD OF TREATING MYOCARDIAL INFARCTION WITH PDE-5 INHIBITORS

Provisional application Ser. No. 60/382,088, filed May 22, 2002 and claims a benefit of U.S. Provisional application Ser. No. 60/402,060, filed Aug. 09, 2002.

This invention was made using funds from grants from the National Institutes of Health having grant numbers HL-51045 and HL-059469. The United States government may have certain rights in this invention.

BACKGROUND OF THE INVENTION

1. Field of the Invention

The invention generally relates to the prevention of ischemia/reperfusion injury. In particular, the invention provides a method of preventing ischemia/reperfusion injury by administering a phosphodiesterase-5 (PDE5) inhibitor such as sildenafil.

2. Background of the Invention

Heart disease remains a leading cause of morbidity and mortality in the United States, affecting approximately 5–6 million Americans, particularly those age 65 and older. In 1995, an estimated $3.4 billion dollars was spent by Medicare for the treatment of heart disease. A continually aging population is expected to result in an increased number of people afflicted with heart-related conditions, requiring costly long-term medical management with an unpredictable affect on quality of life.

Surgical intervention for the treatment of heart disease is widely practiced. In particular, procedures such as coronary bypass and angioplasty are now carried out on a routine basis. However, they are not without inherent risks and the potential for further damage to an already diseased heart. During heart surgery, the heart itself must be temporarily isolated from the circulatory system, and then reperfused with blood following completion of the surgery. This isolation procedure entails the possibility of further damage to the heart and may defeat the purpose of or lessen the benefit of the surgical procedure.

While adenosine is known to cause preconditioning and protection of the heart under these circumstances, it has been determined that the clinical effects are not as promising as those initially reported by experimental studies (Vinten-Johansen et al. 2003). Thus, there is an ongoing need for the discovery of preconditioning agents that afford protection to cells, tissues and organs during periods of potential ischemic injury.

SUMMARY OF THE INVENTION

It is an object of this invention provide a method of treating ischemic/reperfusion injury. The method includes the step of administering to a patient a phosphodiesterase-5 (PDE-5) inhibitor. The PDE-5 inhibitor is administered in an amount sufficient to reduce infarct size in the patient. Administration may be performed prior to or after the ischemic/reperfusion injury occurs, and may be via, for example, intraperitoneal, intravenous, intracoronary or oral routes. Further, the phosphodiesterase-5 inhibitor may be administered in combination with other drugs. The patient may be a human or a non-human mammal.

The invention further provides a method of limiting ischemic/reperfusion damage to a patient's heart. The method includes that step of administering to a patient that has or will undergo an ischemic/reperfusion event a sufficient amount of a phosphodiesterase-5 inhibitor to limit or reduce damage to the patient's heart. Administration may be performed prior to or after the ischemic/reperfusion injury occurs, and may be via, for example, intraperitoneal, intravenous, intracoronary or oral routes. Further, the phosphodiesterase-5 inhibitor may be administered in combination with other drugs. The patient may be a human or a non-human mammal.

The present invention also provides a method of limiting or reducing ischemic/reperfusion damage during surgical procedures. The method includes the steps of performing a surgical procedure on a patient; and administering to the patient a sufficient amount of a phosphodiesterase-5 inhibitor to limit or reduce ischemic/reperfusion damage. The surgical procedure may be, for example, coronary bypass surgery, coronary arteriography, or angioplasty. The administering step may be performed prior to the performing step and may precondition the patient's heart for ischemia/reperfusion. Alternatively, the administering step may be performed after or during the performing step. The surgical procedure may be performed on an organ or tissue such as but not limited to brain, heart, liver, intestine, kidney, lung, gut, spleen, pancreas, nerves, spinal cord, retinal tissue, vasculature, and skeletal muscle. Further, the surgical procedure may be for an organ transplant.

The present invention also provides a method of treating a patient suffering from a heart attack. The method includes the step of administering to the patient a sufficient amount of a phosphodiesterase-5 inhibitor to reduce infarct size in the patient.

The invention further provides a method of upregulating eNOS or iNOS proteins in order to precondition tissue or organs prior to surgical procedures. The method includes the steps of performing a surgical procedure on a patient and administering to the patient a sufficient amount of a phosphodiesterase-5 inhibitor to upregulate eNOS or iNOS proteins and thus precondition the tissue or organ. In a preferred embodiment, the PDE-5 inhibitor is administered prior to said surgical procedure.

The present invention also provides a method to prevent or decrease apoptosis or necrosis caused by an ischemic/reperfusion event in cells, tissues or organs. The method includes the step of comprising the step of exposing the cells, tissues or organs to a sufficient amount of a phosphodiesterase-5 (PDE-5) inhibitor to prevent or decrease apoptosis or necrosis of the cells, tissues or organs. The method may be performed prior to, after, or during the ischemic/reperfusion event. The cells, tissues or organs may located within a patient, and the step of exposing may be performed prior to, during, or after a surgical or interventional procedure. Administration of the PDE-5 inhibitor may be, for example, via intraperitoneal, oral, intravenous, or intracoronary administration to the patient. Further, the method may be used in conjunction with the administration of other drugs. The patient may be a human or a non-human mammal.

In the practice of the methods of the present invention, the amount of PDE-5 inhibitor that is administered may be, for example, about 5 mg or less. In another embodiment, the amount of PDE-5 inhibitor may be about 1 mg or less.

BRIEF DESCRIPTION OF THE DRAWINGS

FIGS. 1A and B: Changes in hemodynamics following intravenous (A) or oral (B) administration of sildenafil citrate. SBP—systolic blood pressure, DBP—diastolic blood pressure; MAP—mean arterial blood pressure. Results are means±SE from 6–7 rabbits.

FIGS. 2A and B: A. Bar diagram showing infarct size (% risk area) after intravenous administration of sildenafil citrate. Saline control—Animals receiving 0.9% saline; Sildenafil (acute phase)—Rabbits receiving sildenafil (0.7 mg/kg, IV) 30 min prior to ischemia/reperfusion; Sildenafil (delayed phase): animals receiving sildenafil (0.7 mg/kg, IV) 24 hrs prior to ischemia/reperfusion. 5-HD—Control (saline-treated) rabbits received 5-HD (5 mg/kg) 10 min prior to sustained ischemia and reperfusion. Sildenafil+5-HD (acute phase): Sildenafil treated rabbits given 5-HD (5 mg/kg, IV) 10 minutes prior to sustained ischemia and reperfusion. Sildenafil+5-HD (delayed phase): Rabbits treated with sildenafil 24 hrs prior to ischemia/reperfusion were given 5-HD. Results are means±SEM in 6–7 rabbits in each group. *P<0.05 compared to control, sildenafil, sildenafil+5-HD (acute and delayed), and 5-HD groups.

B. Reduction of infarct size (% of risk area) after oral administration of sildenafil citrate. Rabbits were given sildenafil (1.4 mg/kg) or equivalent volume of saline prior to ischemia/reperfusion protocol which was carried out after 60 min (acute phase) and 24 hrs later (for delayed phase).

Figure 3:
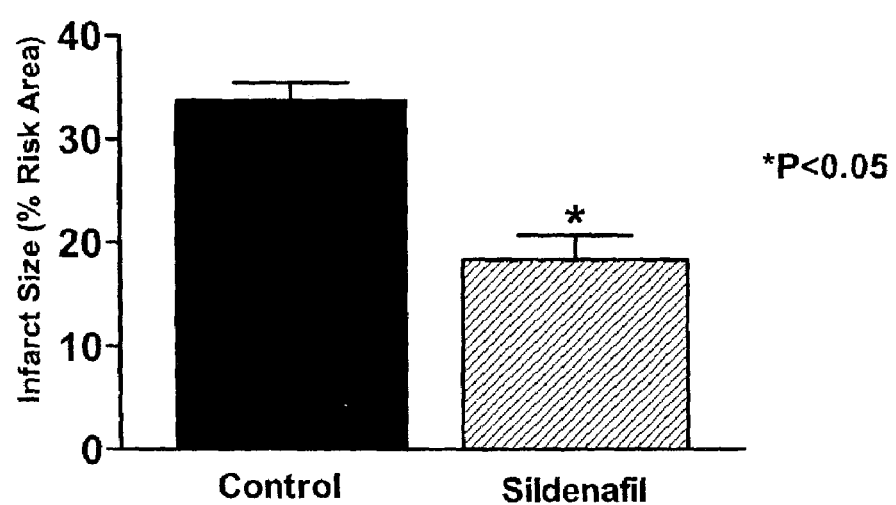
Figure 4:
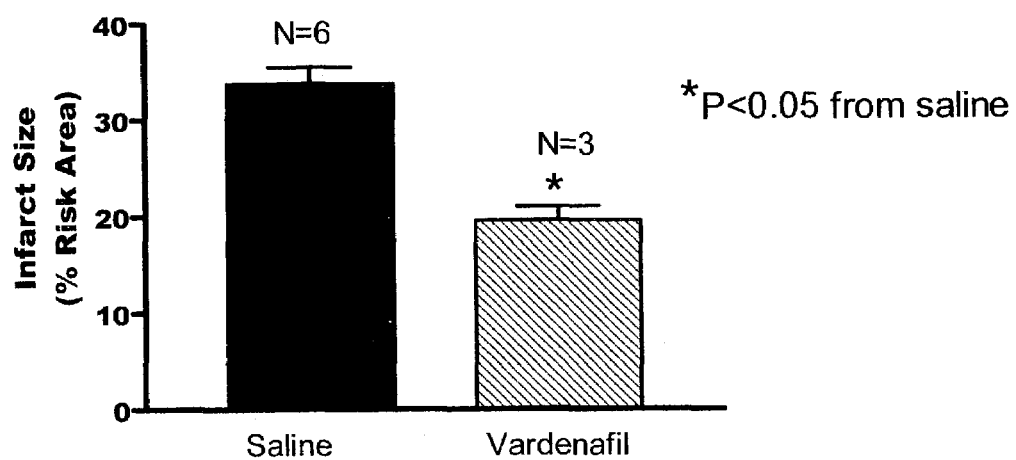

FIG. 3. Results of intravenous administration of Sildenafil (Viagra) to postischemic heart; a significant reduction in the infarct size is shown FIG. 4. Results of intravenous administration of Vardenafil (Lavitra) or equivalent volume of saline prior to ischemiz/reperfusion protocol which was carried out after 30 minutes. A significant reduction in the infarct size is shown.

Figure 5:
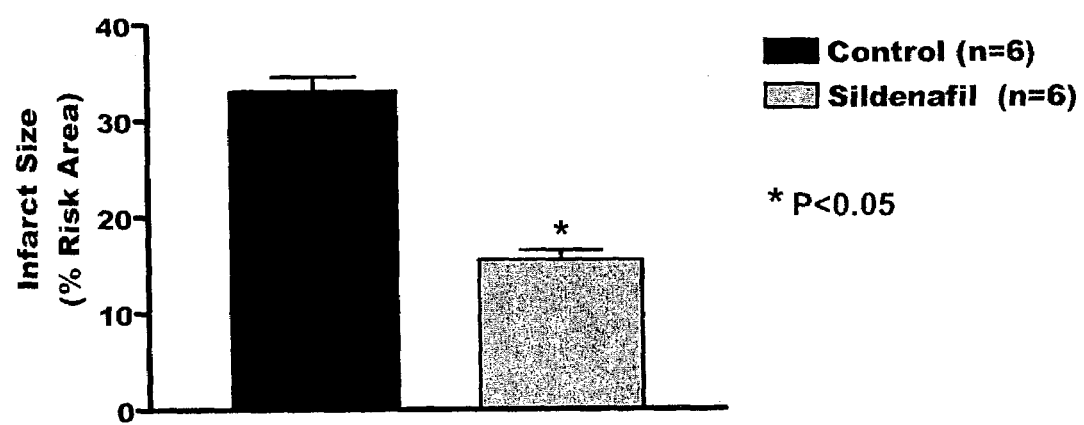

FIG. 5. Results of administration of Sildenafil (Viagra) to infant rabbits; a significant reduction in the infarct size is shown FIGS. 6A and B. Effect of sildenafil and/or 1400W on myocardial infarct size (A) and ventricular functional recovery (B) after global I-R.

Figure 7:
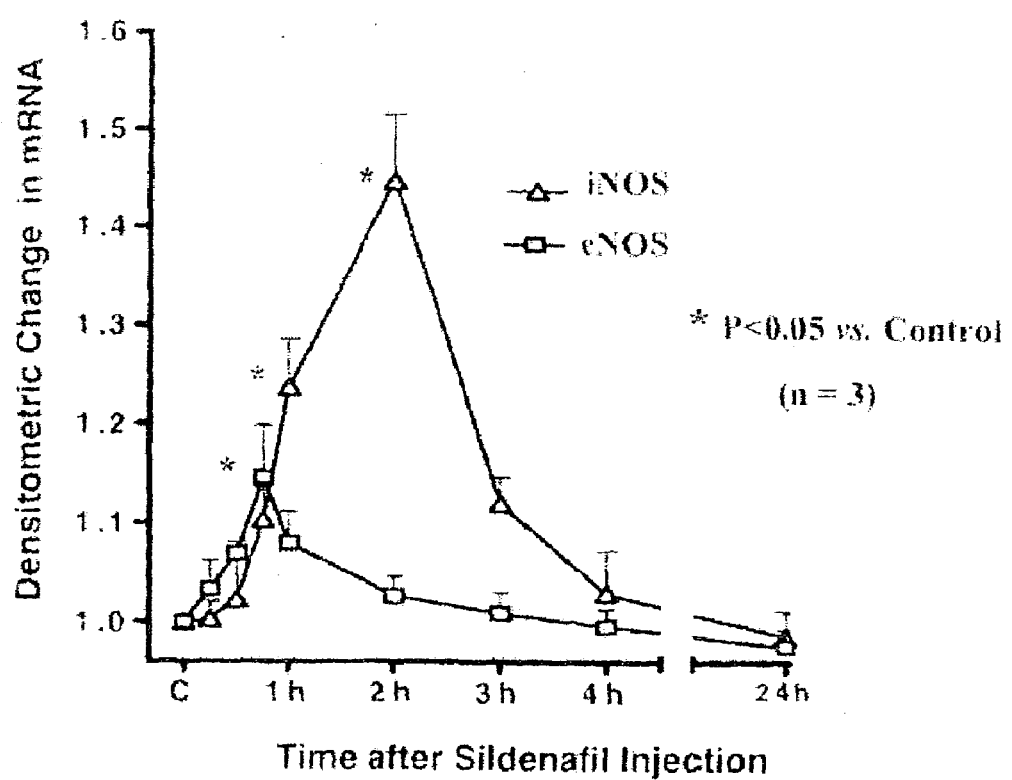

FIG. 7. Time course of iNOS and eNOS mRNA expression determined with RT-PCR after sildenafil treatment. Graph shows densitometric results averaged from 3 individual hearts for each time point, which were normalized against the GAPDH level for each sample.

Figure 8:
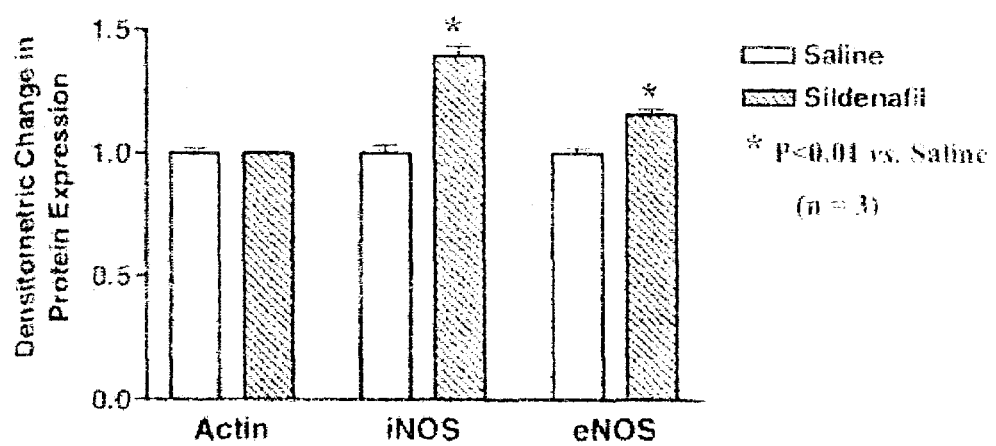

FIG. 8. Cardiac expression of iNOS and eNOS protein 24 hours after sildenafil treatment. Bar graph shows densitometric quantification averaged from 3 individual hearts for each group, which is normalized against the actin level for each sample.

DETAILED DESCRIPTION OF THE PREFERRED EMBODIMENTS OF THE INVENTION

The present invention provides methods for preconditioning cells, tissue or organs in order to prevent injury due to ischemia or ischemia/reperfusion. According to the method, the cells, tissues or organs which will undergo or are at risk of undergoing ischemia/reperfusion are exposed to a phosphodiesterase-5 (PDE-5) inhibitor prior to (and/or during and after) subjection to ischemia/reperfusion. The inventors have discovered that such exposure to a PDE-5 inhibitor prevents or limits damage that would otherwise occur.

By "ischemia" we mean a condition where the blood flow to a tissue or organ is stopped. The stoppage may result from a blockage in the blood vessel supplying the tissue or organ (e.g. during a stroke, or deliberately during surgical procedures), or may result when the heart stops beating (e.g. a heart attack). Reperfusion is the term which describes the restarting of the supply of blood to the organ or tissue following ischemia. By "preconditioning" we mean protection of the heart muscle from serious damage in the future by subjecting it to very brief periods of deprivation of blood flow and, therefore, oxygen. Damage to myocardial tissue from ischemia, decreased oxygenated blood flow to muscle tissue, can be reduced by preconditioning. Ischemic preconditioning (PC) was first described by Jennings and colleagues (Murry et al., 1986). Brief periods (5–10 minutes) of ischemia have been shown to precondition against more prolonged periods of ischemia. Such preconditioning appears to provide protection against greater pathologic effects on myocardial tissue that arise from ischemia compared with tissues not preconditioned.

By "phosphodiesterase-5 (PDE-5) inhibitor" we mean a substance or compound that inhibits (e.g. prevents or decreases) the catalytic activity of the enzyme PDE-5. (For review of phosphodiesterase enzymes and inhibitors, see Rotella, 2002). Typically, an inhibitor is a small molecule (e.g. MW less than about 1000) that binds to an enzyme at its active site or at another site to block the normal activity of the enzyme. Binding may be covalent, ionic, or via hydrogen bonding, or a combination of these, and may be reversible or irreversible.

The enzyme PDE-5 catalyzes the breakdown of the smooth muscle relaxing agent cyclic guanosine monophosphate (cGMP). Inhibitors of PDE-5 for use in the present invention may completely abolish PDE-5 enzymatic activity, or may reduce that activity by at least about 50% to 100%.

Those of skill in the art will recognize that many compounds exist which are inhibitors of PDE-5. Examples include but are not limited to sildenafil, vardenafil, tadalafil, zaprinast, and the like.

In one embodiment of the present invention, the PDE-5 inhibitor that is employed in the practice of the present invention is sildenafil (Viagra). Sildenafil is a potent selective inhibitor of PDE-5 in vascular smooth muscle cells which is known to enhance erectile function in men (Wallis, 1999). Sildenafil is the first oral agent approved for treatment of erectile dysfunction in men (Cheitlin et al., 1999; Kloner and Jarow, 1999; Corbin, 2002). Its method of action is as follows: Sexual stimulation results in the release of NO from nerves and endothelial cells in the corpus cavernosum of the penis, which in turn stimulates guanylate cyclase with subsequent formation of cGMP. Accumulation of cGMP leads to smooth muscle cell relaxation in the arteries, arterioles and sinusoids in the corpus cavernosum, allowing this erectile tissue to fill with blood and causing erection (Kloner, 2000). Men with erectile dysfunction may be unable to maintain adequate amounts of cGMP because it is broken down by PDE-5, which is found in high levels in the genitalia. By inhibiting PDE-5, sildenafil allows an increase in cGMP concentration and improved vasodilation, thus facilitating erection.

Without being bound by theory, in the practice of the present invention, the vasodilatory action of PDE-5 inhibitors such as sildenafil may function by triggering the release of endogenous mediators of preconditioning, leading to protection of cells and/or tissue from ischemic/reperfusion injury.

In another embodiment of the invention, the PDE-5 inhibitor is vardenafil, which is also used for treatment of erectile dysfunction in men.

Those of skill in the art will recognize that many situations exist in which an individual may be at risk for incurring injury due to ischemia/reperfusion. Examples include but are not limited to when an individual undergoes a surgical procedure such as coronary bypass, coronary arteriography, or angioplasty. During such procedures, the heart is subjected to ischemia and reperfusion and, in the absence of preconditioning, is susceptible to injury. According to the methods of the present invention, a PDE-5 inhibitor may be administered to the patient prior to, during, or after such procedure, or at any combination of those times (e.g. before, during and after), in order to prevent or lessen the extent of injury due to ischemia/reperfusion. Administration of PDE-5 inhibitors may serve as an adjunct therapy in, for example, coronary bypass surgery and angioplasty. Examples of other areas in which an individual may be at risk for incurring injury due to ischemia/reperfusion include but are not limited to brain, liver, kidney and other organs.

Further examples of the use of PDE-5 inhibitors according to the present invention include the prophylactic use of PDE-5 inhibitors in persons who are at risk for developing ischemia-related conditions. Preferred ischemic (or potentially ischemic) tissues that may be treated in accordance with the methods of the present invention include but are not limited to brain, cardiac, liver, kidney, lung, gut, skeletal muscle, spleen, pancreas, nerve, spinal cord, retinal tissue, vasculature, and intestinal tissue. An especially preferred tissue is cardiac tissue. Examples of individuals who might benefit from prophylactic treatment with PDE-5 inhibitors include but are not limited to persons with risk factors for the development of such pathological conditions, e.g. those with risk factors such as: a positive family history of ischemic heart disease, a genetic predisposition to develop ischemic heart disease, diabetes, hyperlipidemia, hypertension, obesity, cigarette smoking, sedentary lifestyle, psychosocial tension and certain personality traits (e.g. "type A personality"). Prophylactic administration of a PDE-5 inhibitor results in preconditioning of the cells, tissues and organs exposed thereto and prevents, slows or lessens the extent of the development of ischemic injury.

Those of skill in the art will recognize that, in some cases, ischemic/reperfusion injury may be completely prevented by the administration of PDE-5 inhibitors. However, it is also possible that an individual may obtain great benefit even if complete prevention is not attained, e.g. any lessening or slowing of injury due to ischemia/reperfusion, in comparison to injury sustained without PDE-5 administration, may be of benefit.

The PDE-5 inhibitors used in the practice of the present invention may be administered as a pharmaceutical preparation comprising a pharmaceutically acceptable carrier. Such a pharmaceutical preparation may be in any of many forms known to be suitable for administration of drugs, including but not limited to injectable dosage forms and solid dosage forms such as tablets, capsules, and the like. The PDE-5 inhibitor may be administered in the pure form or in a pharmaceutically acceptable formulation including suitable elixirs, binders, and the like, or as pharmaceutically acceptable salts or other derivatives (e.g. sildenafil citrate). It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintegrating agents, coatings and the like. Preservatives such as methyl paraben or benzalkonium chloride may also be used. Depending on the formulation, it is expected that the active agent (the PDE-5 inhibitor) will consist of 1–99% of the composition and the vehicular "carrier" will constitute 1–99% of the composition. Such pharmaceutical compositions may include any suitable pharmaceutically acceptable additives or adjuncts to the extent that they do not hinder or interfere with the desired therapeutic effect of the PDE-5 inhibitor.

Those of skill in the art will recognize that the exact dosage of the PDE-5 inhibitor to be administered may vary depending on factors such as the age, gender, weight and overall health status of the individual patient, as well as on the precise nature of the condition being treated, and on the exact inhibitor being administered. Similarly, the length of duration of treatment with PDE-5 inhibitor will vary from individual to individual, and will depend on the application and the inhibitor. For example, for prophylaxis against a genetic predisposition, a relatively low dose may be administered over a period of many months or even years in order to maintain protection. However, in order to achieve protection for a specific event such as heart surgery, relatively higher doses may be administered just prior to (e.g. within hours or a few days) and may cease shortly after completion of the surgical procedure (e.g. within hours or a few days). In all cases, the amount of PDE-5 inhibitor to be administered and the precise treatment protocol is determined by a skilled practitioner such as a physician.

Those of skill in the art will recognize that, in general, the preferred dosage of PDE-5 inhibitor required to practice the methods of the present invention, i.e. the quantity sufficient to carry out the method, is significantly less than that which is required for the previously known application of treating male erectile dysfunction (MED). For example, for treatment of MED a typical dosage of sildenafil is in the range of 25 to 100 mg for a 70 kg person. In contrast, to elicit cardioprotective effects, a dose of at most 5–10 mg for a 70 kg individual is effective. In one embodiment, the dosage of PDE-5 inhibitor administered for protection from ischemia/reperfusion injury and for cardioprotection is 5 mg or less. In yet another embodiment, the dosage is 1 mg or less. The administration of lower doses provides advantages such as a lower risk of side effects associated with such administration.

The PDE-5 inhibitor may be administered by any of a wide variety of means which are well known to those of skill in the art, (including but not limited to intravenously, intracoronary, intramuscularly, intraperitoneally, orally, rectally, intraocularly, and the like) or by other routes (e.g. transdermal, sublingual, aerosol, etc.). and may be in any form (e.g. liquid, solid, etc.) which is suitable for the particular means of administration.

Further, the PDE-5 inhibitor may be administered either alone or together with other medications in a treatment protocol. For example, a PDE-5 inhibitor may be administered either separately or in combination with other cardiac drugs such as beta-adrenergic blockers, calcium channel antagonists and/or aspirin; antioxidants; and either separately or in combination with fibrinolytic drugs such as tissue plasminogen activator (tPA), streptokinase and urokinase; or either alone or in combination with other PDE-5 inhibitors.

Those of skill in the art will recognize that many other applications of the method of the present application also exist. For example, the ischmia/reperfusion event need not be of surgical origin but may occur for any of a variety of other reasons. For example, the administration of PDE-5 inhibitors may be beneficial for individuals who are suspected of undergoing or have recently (e.g within about 24 hours or less) undergone a heart attack. In this case, administration of the PDE-5 inhibitor should occur as soon as possible after the condition is recognized. Nevertheless, if administration cannot or does not occur during or soon after a heart attack (e.g. within 24 hours or less), the administration of the PDE-5 inhibitor may still be advantageous due to the delayed cardioprotective effects that PDE-5 inhibitors have been shown to exhibit, as demonstrated herein. For example, administration of a PDE-5 inhibitor may be beneficial for up to about 24 hours or 7 days after the attack. Examples of other applications include but are not limited to treatment of angina pectoris, unstable angina pectoris, angina pectoris after myocardial infarction, myocardial infarction, acute myocardial infarction and coronary restenosis after percutaneous transluminal coronary angioplasty (PTCA), etc.

In one embodiment of the invention, the cells, tissues or organs that are preconditioned and protected from ischemic/reperfusion injury are cardiac in nature. However, those of skill in the art will recognize that many other types of cells, tissues and organs are susceptible to injury due to ischemic/reperfusion and may be protected by the method of the present invention. Examples of other cell/tissue/organ types include but are not limited to brain, liver, kidney, lung, intestine, nerve, spinal cord, gut, skeletal muscle, spleen, pancreas, spinal cord, retinal tissue and vasculature.

In some applications of the methods of the present invention, the cells, tissues or organs that are treated with a PDE-5 inhibitor are located within an individual such as a human patient. However, those of skill in the art will recognize that this need not be the case. For example, it may sometimes be of benefit to treat cells, tissues or organs that have been removed from a donor organism, such as a human or other mammal. The cells, tissues or organs may have been removed or partially removed for any of a variety of reasons, e.g. for a surgical procedure in which they are temporarily completely or partially removed from a patient in order to facilitate the procedure, and then replaced. Alternatively, the cells, tissues or organs may be permanently removed from a donor and used, for example, for the purpose of transplantation to a transplant recipient, or for experimental purposes. Use of the method of the present invention for such purposes will help to maintain viability of transplanted material during transport to the transplant recipient, or of experimental material during experimental procedures. Examples of cells, tissues or organs which can be advantageously treated in this manner include but are not limited to heart, brain liver, kidney, lung, skeletal muscle, spleen, pancreas, retinal tissue and vasculature.

Those of skill in the art will recognize that serious injury due to ischemia or ischemia/reperfusion can occur to both the donor and the recipient during an organ transplant procedure. Thus, prevention and treatment of such injury according to the methods of the present invention may be carried out by administering a PDE-5 inhibitor by any of a variety of different strategies. For example, the inhibitor may be administered: to a transplant donor prior to, during or after removal of the organ/tissue that is being donated; to a transplant recipient prior to, during or after receipt of the organ/tissue that is being donated; or directly to the organ/tissue itself either prior to removal from the donor, after transplantation into the recipient, or during the time after removal and before transplant, e.g. during storage and transportation of the organ/tissue.

While in some embodiments, the cells, tissues or organs that are treated by the methods of the present invention are human in origin, this need not be the case. Those of skill in the art will recognize that the cells, tissues or organs of other mammals may also benefit from the methods of the present invention. Thus, veterinarian and cross-species transplant applications are also contemplated. Further, individuals treated with PDE-5 inhibitors according to the methods of the present invention may be in any stage of life, e.g. new-born, adult, or aging.

Without being bound by theory, it appears that the palliative effects of PDE-5 inhibitors are due at least in part to their ability to open mitochondrial potassium-adenosine triphosphate (mitoK$_{ATP}$) channels. The present invention thus also provides a method of providing preconditioning against ischemia/reperfusion injury in cells, tissues and organs by administering PDE-5 inhibitors in a quantity sufficient to open mitoK$_{ATP}$ channels therein. Thus, the methods of the present invention may serve to prevent cell damage or death due to abnormal mitochondrial function, or to preserve mitochondrial ATP levels and reduce calcium overload during pathophysiological conditions in the heart, brain, and other organs. Examples of such pathophysiological conditions include but are not limited to angina pectoris, unstable angina pectoris, angina pectoris after myocardial infarction, myocardial infarction, acute myocardial infarction, coronary restenosis after PTCA, and stroke.

At the cellular level, ischemic injury is characterized by the death of affected cells. Death of the cells may be due to either necrosis or apoptosis, or both, depending on the availability of ATP to the cells (see discussion re cardiac cells in Example 3). The present invention also provides a method of protecting cells from necrosis and/or apoptosis by exposing the cells to PDE-5 inhibitors. In the Examples below, the efficacy of PDE-5 administration in protecting, for example, cardiac cells from apoptosis is demonstrated.

Doxorubicin (DOX) is a powerful anthracycline antibiotic used to treat many human neoplasms, including acute leukemias, lymphomas, stomach, breast and ovarian cancers, Kaposi's Sarcoma, and bone tumors (Ferrans, 1978). Doxorubicin may also cause dose-dependent cardiotoxicity often leading to irreversible cardiomyopathy and ultimately congestive heart failure. Although recent evidence shows that less toxic doses of doxorubicin can be used effectively, heart failure in doxorubicin-treated patients can go undetected for up to 20 years after treatment cessation, causing some cancerpatients to be unwilling to use doxorubicin (Mettler et al., 1977; Steinharz et al, 1991). This is obviously a serious drawback in the treatment of cancer. However, the present invention provides a solution to this dilemma in that the prophylactic administration of PDE-5 inhibitors to a patient undergoing treatment with DOX prevents or lessens the occurrence of doxorubicin-induced cardiotoxicity.

In yet another aspect of the present invention, the treatment or prevention of ischemic/reperfusion injury during certain interventional procedures is contemplated. In one embodiment, the interventional procedure is that of removal of a clot, for example, by dissolution with drugs. Those of skill in the art will recognize that much of the damage and risk associated with clot dissolution is associated with the influx of blood into the area that was blocked by the clot and thus subjected to ischemia. Tissues or cells subjected to ischemia undergo changes that make them particularly vulnerable to injury by, for example, inflammatory cells in the blood that is reintroduced. Thus, one aspect of the present invention is to treat or prevent injury associated with ischemia/reperfusion that occurs as a result of clot removal. The treatment involves administration of a PDE-5 inhibitor in a quantity sufficient to prevent or lessen damage to cells, tissues, or organs that are affected by the presence and subsequent removal of the clot.

EXAMPLES

Example 1

Cardioprotective Effect of Sildenafil Citrate

Background

Sildenafil citrate (Viagra) is the first oral agent approved for treatment of erectile dysfunction in men (Cheitlin et al., 1999; Kloner and Jarow, 1999). It is a selective inhibitor of phosphodiesterase-5 (PDE-5), an enzyme that catalyzes the breakdown of a potent smooth muscle relaxing agent cyclic guanosine monophosphate (cGMP). Sildenfil has been shown to enhance nitric oxide (NO)-driven cGMP accumulation in the corpus cavernosum of rabbits without affecting cAMP formation. In the absence of NO drive, sildenafil had no functional effect on the human and rabbit isolated corpus cavemosum, but potentiated the relaxant effects of NO on these tissues (Wallis, 1999). Also, it has been shown that sildenafil causes mild to moderate decreases in systolic and diastolic pressure because of the inhibition of PDE-5 in smooth muscles in the vascular bed (Kloner and Zusman, 1999).

In the present studies, the ability of sildenafil to trigger preconditioning in coronary vasculature was tested. Since opening of the mitochondrial $K_{ATP}$ (mito$K_{ATP}$) channel mediates the cardioprotective effect of preconditioning induced by adenosine (Auchampach and Gross, 1993; Baxter and Yellon, 1999; Bemado et al., 1999a; and Cohen et al., 2000) or sublethal ischemia (Bernado et al., 1999b), these channels could potentially be involved in the cardioprotective effect of sildenafil. Accordingly, the goals of the present study were: (a) to show that the sildenafil induces both acute and delayed protection against ischemia/reperfusion injury in vivo and (b) to demonstrate if the protective effect of this drug is blocked by 5-hydroxydecanoate (5-HD), a selective blocker of mito$K_{ATP}$ channel (Liu et al., 1998). Using an in situ rabbit model of myocardial infarction, sildenafil induced acute and delayed cardioprotective effects, which are dependent on the opening of mito$K_{ATP}$ channels, were for the first time demonstrated.

Methods

Animals. Male New Zealand White rabbits (2.8 to 3.3 kg) were used for the studies. The care and use of the animals were conducted in accordance with the guidelines of the Committee on Animals of Virginia Commonwealth University and the National Institute of Health (NIH) "Guide for the Care and Use of Laboratory Animals" [DHHS Publication No. (NIH) 80-23, Revised, Office of Science and Health Reports, Bethesda, Md. 20205].

Surgical procedure: Infarction protocol. The rabbits were anesthesized with an intramuscular injection of ketamine HCl (35 mg/kg) and xylazine (5 mg/kg). Subsequent doses of ketamine-xylazine (10 mg/kg and 2 mg/kg, respectively) were administered during the experiment as needed to maintain surgical anesthesia. Atropine was administered along with the anesthetic in order to keep the heart rate elevated especially during the surgery protocol. The body temperature was monitored and maintained at 38° C. throughout the experimental protocol. The neck was opened with a ventral midline incision and tracheotomy performed followed by intubation. The animal was then mechanically ventilated on a positive pressure ventilator using compressed room air at 30–35 cycles/min with a tidal volume of approximately 15 ml. Ventilator setting and $pO_2$ were adjusted as needed to maintain the arterial blood gas parameters within the physiological range. The blood gases and pH were measured 12 times for all the groups during the infarction protocol. The arterial blood gases and pH values ranged between 7.20 and 7.50 with $pCO_2$ maintained between 20 and 50 mmHg and the $HCO_3$ level ranging between 15.0 and 28.0 mg/L. The $pO_2$ ranged between 60 and 150 mmHg with the saturation constantly kept above 90%. The jugular vein was cannulated with a polyethylene (PE) catheter for continuous infusion of 0.9% saline solution. The carotid artery likewise was dissected and cannulated with a PE catheter for blood sampling and continuous arterial pressure monitoring. Electrocardiographic leads were attached to subcutaneous electrodes to monitor either limb lead II or lead III.

Following stabilization of the hemodynamics, a left thoracotomy was performed through the fourth intercostal space and the pericardium opened to expose the heart. A 5-0 silk suture with a traumatic needle was then passed around the left anterior descending artery (LAD) midway between the atrioventricular groove and the apex. The ends of the tie were then threaded through a small vinyl tube to form a snare. To induce infarction, the LAD was occluded for 30 min by pulling the snare and then fixing it in place by clamping the vinyl tube with a hemostat. A bolus of heparin sodium 500 IU was given immediately before coronary occlusion for prophylaxis against thrombus formation around the snare. Myocardial ischemia was confirmed visually in situ by regional cyanosis, ST elevation/depression or T wave inversion on electrocardiogram, hypokinetic/dyskinetic movement of the myocardium, and relative hypotension. After 30 min of ischemia, the snare was released and the heart allowed to reperfuse for 180 min. This was readily confirmed by hyperemia over the surface of the previously ischemic-cyanotic segment. The thoracic cavity was covered with the saline-soaked gauze to prevent the heart from drying.

Measurement of Infarct Size. Following completion of ischemia/reperfusion protocol, 500 units of heparin was injected and the heart was removed quickly and mounted on a Langendorff apparatus. The coronary arteries were perfused with 0.9% saline containing 2.5 mM $CaCl_2$. After the blood was washed out, the ligation around the coronary artery was re-tightened and approximately 2 ml of 10% Evan's blue dye injected as a bolus into the aorta until most of the heart turned blue. The hearts were then perfused with saline to washout the excess Evan's blue, removed from the Langendorff apparatus, frozen and cut into 4 to 6 transverse slices from apex to base of equal thickness (~1 mm). The slices were then incubated in 1% TTC (triphenyltetrazolium chloride) solution in isotonic pH 7.4 phosphate buffer at 37° C. for 20 minutes. TTC reacts with NADH in the presence of dehydrogenase enzymes causing the cells viable to stain with a deep red color. Red-stained viable tissue was easily distinguished from the infarcted gray or white-unstained necrotic tissue. The slices were subsequently fixed in 10% formalin solution. The area at risk was determined by negative staining with Evan's blue. The areas of infarcted tissue, the risk zone, and the whole left ventricle (LV) were measured by computer morphometry using a Bioquant imaging software (BIO98). Infarct size was expressed both as a percentage of the ischemic risk area.

Measurement of hemodynamics. Hemodynamic measurements included heart rate and mean arterial pressure, systolic and diastolic blood pressure. Rate-pressure product was calculated as the product of heart rate and peak arterial pressure.

Study Protocol. All animals were subjected to infarction protocol consisting of 30 minutes of sustained ischemia by occlusion of coronary artery followed by 180 minutes of reperfusion. The effect of sildenafil was studied in the absence or presence of 5-HD in two phases i.e., the acute and delayed phase. In the acute phase, myocardial infarction protocol was carried out 30 min after treatment with sildenafil. In the delayed phase, ischemia/reperfusion protocol was carried out 24 hours later. The rabbits were randomly assigned into one of the following groups.

Following is the description of the experimental groups:

Group I: (saline control, n=10): Rabbits received 0.9% saline;

Group II: (Sildenafil, acute phase, n=6): The Viagra tablets were crushed and 0.7 mg/kg sildenafil was dissolved in 3 ml saline. This preparation was given as IV bolus, approximating on a mg/kg basis, the clinical dose of 50 mg administered to a 70 kg patient as described by Przyklenk and Kloner (2001). The animals were subjected to ischemia/reperfusion 30 minutes later.

Group III: (Sildenafil, delayed phase, n=6). Animals were treated with sildenafil as in group II and subjected to ischemia/reperfusion 24 hrs later;

Group IV: (5HD, n=7). Control rabbits treated with 5-HD (5 mg/kg, IV) 10 min prior to sustained ischemia and reperfusion;

Group V: (Sildenafil, +5HD, acute phase, n=6). Sildenafil treated rabbits as in group II were given 5-HD (5 mg/kg, IV) 10 min prior to ischemia and reperfusion;

Group VI: (Sildenafil,+5HD, delayed phase, N=6). Sildenafil treated rabbits as in group III were given 5-HD (5 mg/kg, IV) 10 min prior to ischemia and reperfusion.

In addition, a subset of three groups of animals (n=5–6 per group) were given sildenafil citrate orally (1.4 mg/kg) or saline (control) in order to determine the early and delayed cardioprotective effect of the drug through this route. Since there is 40% bioavailability of sildenafil citrate after oral administration (Pfizer home page at pfizer.com) double the dose of intravenous route was used, i.e., 1.4 mg/kg which is equivalent to clinical dose of 100 mg for a 70 kg patient.

Statistics. All measurements of infarct size and risk areas are expressed as group means±SEM. Changes in hemodynamics and infarct size variables were analyzed by a two-way repeated measure ANOVA to determine the main effect of time, group and time by group interaction. If the global tests showed major interactions, post hoc contrasts between different time-points within the same group or between different groups were performed using t-test. Statistical differences were considered significant if p value was less than 0.05.

Results

Intravenous administration of sildenafil citrate (0.7 mg/kg) caused rapid decrease in hemodynamics as indicated by 24.5%, 47.3% and 38.8% decline in systolic, diastolic and mean arterial pressure respectively within 2 minutes (FIG. 1A). The systemic hemodynamics returned to nearly baseline levels by 5 minutes after treatment with sildenafil. No significant changes in heart rate were observed following treatment with sildenafil (not shown). The effect of orally administered sildenafil citrate on systemic hemodynamics was milder and slower as compared to the intravenous dose of the drug. The orally administered sildenafil caused approximately 9.2%, 12.5% and 10.3% decrease in systolic, diastolic and mean arterial pressure respectively after 30 minutes of treatment with the drug (FIG. 1B). This hypotensive response remained significant even at 60 minutes after oral administration of drug. No changes in heart rate were observed. Also, no significant changes in systemic hemodynamics were observed in control animals given saline orally (data not shown). The heart rate, mean arterial pressure and rate pressure product during baseline, preischemia, 30 min of ischemia and 180 min of reperfusion period are shown in Tables 1 and 2. The hemodynamics remained reasonably stable, although they gradually decreased in all the groups during experimental protocol. Except at the indicated time points, the mean values were not significantly different between the groups at any time point.

The results showed that infarct size (% of risk area) reduced from 33.8±1.7 in the saline treated control group to 10.8±0.9 during acute phase (68% reduction, mean±SE, p<0.05) and 19.9±2.0 during delayed phase (41% reduction) in the sildenafil-treated rabbits (FIG. 2A). A similar reduction in infarct size was observed acutely (after 60 min) and 24 hrs later when sildenafil was administered orally (Figure B). The infarct-limiting effect of sildenafil was abolished in animals treated with 5-HD as shown by significant increase in infarct size to 35.6±0.4 during acute phase and 36.8±1.6 in the delayed phase (p<0.05 versus groups II and III treated with sildenafil, FIG. 2A). Control animals treated with 5-HD had an infarct size of 33.5±1.9 which was not different from infarct size of 33.8±1.7 in the saline controls (P>0.05). A similar trend in the changes in infarct size was observed when expressed as a percentage of the left ventricle (not shown). Similarly, the risk areas expressed as percentage of left ventricle were not statistically significant different between the groups.

These data suggest that changes in the infarct size observed among various groups were not related to the percentage of the area of the left ventricle that was occluded by our technique.

At the end of experimental protocol as described in Methods, the hearts were perfused with Evan's blue to demarcate the risk area. Each heart was then sliced into 4–5 sections and stained with TTC followed by fixation in formalin. With this technique, viable areas of the heart stain brick red whereas infracted areas are gray or white. Representative sections of the heart treated with sildenafil citrate intravenously clearly showed significantly larger areas of viable tissue, demonstrating reduction of post-ischemic infarct size 30 minutes following treatment with sildenafil. This is in comparison to saline treated control and sildenafil+ 5-HD treated animals, which had much larger gray and white areas in the risk zone (data not shown). A similar pattern was observed in the sections of the heart from the delayed phase groups (not shown).

Discussion

Sildenafil citrate (Viagra) is currently the only approved oral drug for treatment of erectile dysfunction in men. However, little is known about other beneficial effects of this drug. These experiments describe the novel observation about the preconditioning-like effect of sildenafil in the adult rabbit heart. The results show that intravenous administration of sildenafil induces acute (early) and delayed cardioprotective effect as indicated by significant reduction in the infarct size when compared to the saline-treated controls. Since the drug is taken orally by patients, it was further shown that feeding the rabbits with sildenafil citrate reduced infarct size acutely (after 1 hr) as well as 24 hrs later which was comparable to the infarct size reduction obtained by intraveous administration of the drug. The selective blocker of mitoK$_{ATP}$ channels, 5-HD, when administered before the ischemia/reperfusion protocol, abolished both the early as well as delayed cardioprotection induced by sildenafil citrate. Intravenous administration of sildenafil citrate caused severe transient decrease in the systemic hemodynamics (diastolic, systolic and mean arterial blood pressure) within 2 minutes after treatment returned to nearly baseline levels after 3 minutes. Although a significant decrease in systemic hemodynamics was also observed after oral administration of the drug, these changes were mild and occurred slowly. The hemodynamics remained largely unchanged among the groups during ischemia/reperfusion protocol. This is the first study demonstrating (a) the direct cardioprotective effect of sildenafil in vivo and (b) the involvement of mitoK$_{ATP}$ channel in mediating this protection in the ischemic heart.

Sildenafil is a potent selective inhibitor of PDE-5 in vascular smooth muscle cells which is known to enhance erectile function in men (Wallis, 1999). Sexual stimulation results in the release of NO from nerves and endothelial cells in the corpus cavernosum of the penis that stimulates guanylate cyclase with subsequent formation of cGMP. Accumulation of cGMP leads to smooth muscle cell relaxation in the arteries, arterioles and sinusoids in the corpus cavernosum that allow this erectile tissue to fill with blood and causing erection (Kloner, 2000). Men with erectile dysfunction may be unable to produce adequate amounts of cGMP because it may be broken down by PDE-5, which is found in high levels in the genitalia. Sildenafil inhibits PDE-5 allowing an increase in cGMP and improving vasodilation. Besides genitalia, PDE-5 is found in other vascular and visceral smooth muscles also (Wallis et al., 1999). As a result, the administration of sildenafil causes vasodilation and decrease in the blood pressure. Without being bound by theory, such a vasodilatory action of sildenafil could potentially release endogenous mediators of preconditioning such as adenosine, bradykinin or NO. One or more of these mediators may trigger a signaling cascade leading to opening of mitoK$_{ATP}$ channel resulting in acute and delayed cardioprotective effect. Indeed our results show a very impressive acute cardioprotective effect which is comparable or even better than ischemic preconditioning (Ytrehus et al., 1994) and pharmacological preconditioning induced by activation of adenosine receptors, monophosphoryl lipid A or bradykinin (Janin et al., 1998; Kositprapa et al., 2001; Takano et al., 2001; Yao et al., 1993; Yoshida et al., 1996).

The cardioprotective effect after 24 hrs was less pronounced during delayed phase i.e., 41% reduction of infarct size as compared to 67% in the acute phase (% risk area) implying that there may be gradual waning of the sustained protective effect. Alternatively, it is possible that sildenafil-induced protection is biphasic, with acute and delayed phase protection controlled by separate mechanisms.

Another interesting observation in the present study is that both acute and delayed cardioprotective effects were blocked by 5-HD suggesting that opening of mitoK$_{ATP}$ channels play an important role in the infarct size reduction by sildenafil in our model. Several studies have now conclusively demonstrated that opening of mitoK$_{ATP}$ channels play an important role in ischemic as well as pharmacological preconditioning in the heart (Fryer et al, 1999; Gross and Fryer, 2001; Takashi et al, 1999; Wang et al., 2001). Mitochondria are known to play an essential role in cell survival by ATP synthesis and maintenance of Ca$^{2+}$ homeostasis. Opening of the mitoK$_{ATP}$ channel partially compensates the membrane potential, which enables additional protons to be pumped out to form a H$^+$ electrochemical gradient for both ATP synthesis and Ca$^{2+}$ transport (Szewczyk, 1996). The acute protection induced by sildenafil may be mediated by opening of the mitoK$_{ATP}$ channel either directly or through a variety of signaling pathways such as activation of protein kinase C and MAP kinases. The delayed phase could be through the signaling cascade leading to the synthesis of inducible nitric oxide synthase, generation of NO and opening of the mitoK$_{ATP}$ as described previously (Tejero-Taldo et al, 2002; Xi et al. 1999a; Xi et al. 1999b; Zhao et al. 2000; Zhao and Kukreja, 2002; Zhoa et al. 2001)

These studies demonstrate that intravenous or oral administration of sildenafil citrate induces significant cardioprotective effects against ischemia/reperfusion injury, the impact of which was powerful within 30 minutes and persisted to slightly lesser degree 24 hrs after administration of the drug. The extent of protection observed with sildenafil was comparable to preconditioning induced by sublethal ischemia and several other pharmacological agents. Furthermore, our results show that the cardioprotective effect of sildenafil was mediated by opening of mitoK$_{ATP}$ channels, a proposed end-effector of myocardial preconditioning (Gross and Fryer, 2001; Wang et al., 2001).

TABLE 1

Hemodynamic data during ischemia/reperfusion following intravenous administration of sildenafil.

| Group | Baseline | Preischemia | 30-min Ischemia | Reperfusion (60 min) | Reperfusion (120 min) | Reperfusion (180 min) |
|---|---|---|---|---|---|---|
| Group I Saline Control n = 10 | | | | | | |
| HR | 193 ± 8$^d$ | 197 ± 8 | 197 ± 9 | 183 ± 10 | 173 ± 9 | 165 ± 9 |
| MAP | 92 ± 2$^{d,e,f}$ | 87 ± 5$^f$ | 79 ± 3$^a$ | 71 ± 2$^{a,b,f}$ | 69 ± 3$^{a,b,f}$ | 67 ± 2$^{a,b,e,f}$ |
| RPP | 19,684 ± 1082 | 19,506 ± 818 | 17,567 ± 588$^e$ | 15,127 ± 867$^{a,b,c}$ | 13,952 ± 784$^{a,b,c}$ | 12,677 ± 711$^{a,b,c}$ |
| Group II Sildenafil, acute phase, n = 6 | | | | | | |
| HR | 247 ± 20 | 204 ± 8 | 208 ± 11 | 201 ± 14 | 177 ± 11$^a$ | 158 ± 12$^a$ |
| MAP | 77 ± 4$^f$ | 81 ± 6$^f$ | 76 ± 7 | 76 ± 5$^f$ | 74 ± 5$^f$ | 73 ± 5$^f$ |
| RPP | 21,988 ± 2129 | 18,132 ± 999 | 17,728 ± 1441 | 16748 ± 1425 | 14909 ± 1289$^a$ | 12,967 ± 1115$^a$ |
| Group III Sildenafil, delayed phase, n = 6 | | | | | | |

TABLE 1-continued

Hemodynamic data during ischemia/reperfusion following intravenous administration of sildenafil.

| Group | Baseline | Preischemia | 30-min Ischemia | Reperfusion (60 min) | Reperfusion (120 min) | Reperfusion (180 min) |
|---|---|---|---|---|---|---|
| HR | 229 ± 14 | 215 ± 8 | 189 ± 8$^a$ | 179 ± 8$^{a,b}$ | 170 ± 8$^{a,b}$ | 164 ± 11$^{a,b}$ |
| MAP | 76 ± 5$^f$ | 71 ± 5$^f$ | 73 ± 9 | 74 ± 9$^f$ | 73 ± 5$^f$ | 68 ± 3$^f$ |
| RPP | 19,692 ± 1528 | 17,764 ± 1174 | 15,395 ± 1784 | 15,086 ± 1989 | 13,477 ± 1285$^a$ | 12,196 ± 1088$^a$ |
| Group IV. 5-HD, n = 7 | | | | | | |
| HR | 171 ± 13$^{d,e}$ | 178 ± 13 | 185 ± 8 | 162 ± 8 | 160 ± 8 | 160 ± 7 |
| MAP | 120 ± 4 | 110 ± 6 | 95 ± 5$^a$ | 97 ± 5$^a$ | 91 ± 5$^a$ | 91 ± 7$^a$ |
| RPP | 22477 ± 1849 | 20977 ± 1373 | 19215 ± 999 | 17050 ± 1132 | 15770 ± 984$^a$ | 16300 ± 1503$^a$ |
| Group V. Sildenafil+5-HD, acute phase, n = 6 | | | | | | |
| HR | 215 ± 9 | 203 ± 5 | 187 ± 7$^a$ | 173 ± 7$^{a,b}$ | 166 ± 6$^{a,b}$ | 160 ± 10$^{a,b}$ |
| MAP | 86 ± 2$^f$ | 86 ± 2$^f$ | 81 ± 5 | 76 ± 4$^f$ | 71 ± 4$^{a,f}$ | 67 ± 3$^{a,f}$ |
| RPP | 22384 ± 1041 | 21527 ± 1244 | 17133 ± 1518$^{a,b}$ | 14801 ± 1171$^{a,b}$ | 13371 ± 1030$^{a,b}$ | 12040 ± 1019$^{a,b,c}$ |
| Group VI. Sildenafil+5-HD, delayed phase, n = 6 | | | | | | |
| HR | 190 ± 4$^d$ | 190 ± 5 | 168 ± 7$^{a,b,d}$ | 152 ± 6$^{a,b,d}$ | 139 ± 7$^{a,b,c}$ | 133 ± 5$^{a,b,c}$ |
| MAP | 94 ± 5$^{d,e,f}$ | 92 ± 6$^f$ | 64 ± 3$^{a,b,f}$ | 61 ± 3$^{a,b,f}$ | 63 ± 3$^{a,b,f}$ | 59 ± 3$^{a,b,f}$ |
| RPP | 19,504 ± 786 | 18,955 ± 1058$^a$ | 13,492 ± 756$^{a,b,f}$ | 11,735 ± 593$^{a,b}$ | 10,355 ± 428$^{a,b,c,d,f}$ | 9,299 ± 477$^{a,b,c,d,f}$ |

Values are mean ± SEM. HR-Hear Rate (beats/min); MAP-Mean Arterial Pressure (mmHg); RPP-Rate Pressure Product (systolic arterial pressure × HR);
$^a$P < 0.05 vs. Baseline; $^b$P < 0.05 vs. Preischemia; $^c$P < 0.05 vs. 30-min ischemia; $^d$P < 0.05 vs. Sildenafil acute; $^e$P < 0./05 vs. Sildenafil delayed; $^f$P < 0.05 vs. 5-HD.

TABLE 2

Hemodynamic data during ischemia/reperfusion following oral administration of sildenafil citrate.

| Group | Baseline | Preischemia | 30-min Ischemia | 60-min Reperfusion | 120-min Reperfusion | 80-min Reperfusion |
|---|---|---|---|---|---|---|
| Control (saline) | | | | | | |
| HR | 199 ± 8 | 213 ± 0 | 209 ± 9 | 191 ± 10 | 182 ± 10 | 179 ± 10 |
| MAP | 94 ± 3$^a$ | 84 ± 4$^{a,b,c}$ | 79 ± 4$^{a,b,c}$ | 73 ± 3$^{a,b,c}$ | 72 ± 3$^{a,c}$ | 67 ± 2$^{a,c,d}$ |
| RPP | 21072 ± 950 | 20896 ± 842 | 19067 ± 781 | 16138 ± 855$^{a,b,c,d,}$ | 15342 ± 978$^{c,d,e}$ | 13969 ± 819$^{a,b,c,d}$ |
| Sildenafil (Acute) | | | | | | |
| HR | 216 ± 5 | 210 ± 20 | 216 ± 18 | 205 ± 14 | 187 ± 9 | 187 ± 9 |
| MAP | 100 ± 2a | 95 ± 3 | 96 ± 6 | 89 ± 0.4 | 82 ± 5c | 81 ± 5c |
| RPP | 24859 ± 239 | 22848 ± 2027 | 23137 ± 1617 | 21647 ± 2274 | 17738 ± 860c | 18555 ± 1336 |
| Sildenafil (Delayed) | | | | | | |
| HR | 187 ± 15 | 193 ± 7 | 190 ± 18 | 185 ± 14 | 171 ± 15 | 173 ± 16 |
| MAP | 109 ± 3 | 99 ± 3 | 104 ± 5 | 103 ± 8 | 94 ± 8 | 94 ± 8 |
| RPP | 22626 ± 2173 | 21938 ± 989 | 22089 ± 2288 | 20955 ± 1469 | 17692 ± 978 | 18838 ± 1913 |

Values are means ± SEM. HR-Hear Rate (beats/min); MAP-Mean Arterial Pressure (mmHg); RPP-Rate Pressure Product (systolic arterial pressure x HR);
$^a$P < 0.05 vs. Sildenafil delayed; $^b$P < 0.05 vs. Sildenafil acute; $^c$P < 0.05 vs. Baseline; $^d$P < 0.05 vs. Preischemia; $^e$p < 0./05 vs 30-min ischemia; $^f$P < 0.05 vs. 5-HD.

Example 2

Reduction of Infarct Size following Infusion of Sildenafil (Viagra) During End of Ischemia and Reperfusion In continuation of experiments on the cardioprotective effect of Viagra in rabbit hearts (see Example 1), the effect of sildenafil on reduction of infarct size following its infusion during end of ischemia and reperfusion was tested. Rabbits were anesthetized and subjected to ischemia by occlusion of coronary artery for 30 min followed by reperfusion for 3 hrs as described for Example 1. Sildenafil (total dose 0.7 mg/kg) was infused beginning at 25 min of ischemia and continuing into reperfusion for 1 hr. At the end of reperfusion (3 hrs), the hearts were removed and infarct size was measured by TTC staining. The results showed a significant reduction in infarct size (18.37±2.42, mean±SEM, n=6) in the sildenafil treated group as compared to the saline group (33.76±1.72, mean±SEM, n=6, FIG. 3).

This example demonstrates that Sildenafil induces a cardioprotective effect when given after onset of ischemia.

Example 3

Sildenafil Protects Against Necrosis and Apoptosis Following Ischemia/Reoxygenation in Cardiac Myocytes Background Etiologies of heart failure development are numerous and involve complex molecular mechanisms, not completely understood. However, recent advances have expanded our knowledge and understanding of the cellular and molecular mechanisms involved in the development of heart failure. Numerous studies involving both in vitro and in vivo models of have substantiated the evidence linking reduced oxygen species (ROS) to cardiomyocyte apoptosis (Koning et al., 1991). Apoptosis, commonly known as programmed cell death, is a regulated cellular process dependant on ATP that results in cell death for reasons that often are required in maintaining normal physiological function in many species (Wallis, 1999). For example, apoptosis is involved in the normal, regular, process of intestinal epithelial cell removal required for normal gastrointestinal function (Ockaili et al., 2002). However, it has also been implicated in many pathological processes that often times are prevented from causing significant organ damage via the body's inherent ability at blocking this process (American Heart Association statistics, 2003). Distinguishing apoptotic cell death from DNA repair mechanisms has remained controversial. Apoptosis is recognized by a series of well-defined morphological changes that differ from necrotic cell death. In apoptosis, common morphological findings include condensed heterochromatin often observed in the perinuclear regions of the cardiomyocyte, cell shrinkage, nuclear pyknosis, and late fragmentation into apoptotic bodies (Ide et al., 2000). In contrast, necrotic cell death is characterized by cell membrane disruption and release of intracellular contents that are toxic to surrounding cells and tissues (Kumar et al., 2001). It is hypothesized that apoptosis contributes to the development of heart failure via several mechanisms that contribute to a loss of cardiomyocytes over time, leading to structural changes that often are maladaptive to normal cardiac physiological demands (Keizer et al, 1990). Furthermore, it is also suggested that the major difference between whether cells undergo apoptosis versus necrosis is the cellular availability of ATP. Since apoptosis is an energy-dependent process requiring ATP, cells originally destined for programmed cell death may undergo necrotic cell death if depleted of adequate ATP stores (von Harsdorf et al., 1999).

Methods

The ability of sildenafil to confer protection against necrosis and apoptosis in cardiac myocytes was tested. Freshly isolated myocytes from adult mice were exposed to simulated ischemia with or without sildenafil (10 µM) for 40 minutes followed by reoxygenation for 60 minutes. The ischemic buffer contained (in mM): 118 NaCl, 24 NaHCO$_3$, 1.0 NaH$_2$PO$_4$, 2.5 CaCl$_2$-2H$_2$O, 1.2 MgCl$_2$, 20 sodium lactate, 16 KCl, 10 2-deoxyglucose (pH adjusted to 6.2). At the end of this protocol, necrotic cell death was evaluated by uptake of trypan blue using a phase contrast microscope. To determine apoptosis, the myocytes were reoxygenated for an extended period of 18 hrs after incubating them in the ischemic buffer for 40 minutes. Apoptosis was determined using the terminal deoxynucleotide nick-end labeling (TUNEL) assay which detects cells undergoing programmed cell death due to DNA fragmentation.

Results

An analysis of the results by phase contrast microscopy showed that myocytes exposed to ischemic buffer alone lost their rod-shape morphology when compared to the cells which were subjected to ischemia in the presence of 10 µM sildenafil (results not shown). The cells in the sildenafil treated group had significantly more blue (i.e. viable) cells compared to the non-sildenafil treated group, where the majority of the myocytes did not take up the typan blue because they had been protected (not shown).

TUNEL staining of the control and sildenafil-treated myocytes was carried our after the two groups of cells had been subjected to 40 min of simulated ischemia and 18 hrs of reoxygenation. The results showed significantly more TUNEL positive nuclei (indicative of DNA fragmentation) in the ischemic control group compared to the sildenafil-treated group, indicating that sildenafil rescues myocytes against apoptotic cell death due to simulated ischemia.

These results show that sildenafil induces a robust protective effect in myocytes against necrosis and apoptosis induced by ischemia.

Example 4

Prevention of Doxorubicin-Induced Cardiomyopathy with Sildenafil Citrate

Background

Doxorubicin (DOX) is a powerful anthracycline antibiotic used to treat many human neoplasms, including acute leukemias, lymphomas, stomach, breast and ovarian cancers, Kaposi's Sarcoma, and bone tumors (Ferrans, 1978). Doxorubicin may also causes dose-dependent cardiotoxicity often leading to irreversible cardiomyopathy and ultimately congestive heart failure. Although recent evidence shows that less toxic doses of doxorubicin can be used effectively, heart failure in doxorubicin-treated patients can go undetected for up to 20 years after treatment cessation, causing some cancer patients to be unwilling to use doxorubicin (Mettler et al., 1877; Steinherz et al., 1991). Several hypotheses have been suggested to explain the acute and chronic cardiotoxicity of DOX; these include formation of free radicals, inhibition of enzymes and proteins, changes in cardiac muscle gene expression, alterations of mitochondrial membrane function, sensitization of Ca$^{2+}$ release from sarcoplasmic reticulum channels, mitochondrial DNA damage and dysfunction. Numerous free radical scavengers, such as probucol, amifostine, and dexrazoxane, have been shown to protect the heart against DOX-induced cardiotoxicity (Allen, 1992; Zhang et al., 1996). Unfortunately, all of these scavengers have pronounced clinical disadvantages. Probucol, a lipid-lowering antioxidant, confers significant protection against DOX-induced cardiotoxicity (Allen, 1992); however, concerns about its high-density lipoprotein-lowering property discourage its application in cancer patients. The cytoprotective drug amifostine is less potent than dexrazoxane (Zinecard), an iron chelator, and it does not prevent the mortality and weight loss caused by DOX in spontaneously hypertensive rats (Zhang et al., 1996). Finally, dexrazoxane, the only cardioprotective drug currently available clinically, only reduces 50% of DOX-related cardiac complications (Singal 1998). Moreover, it interferes with the antitumor activity of anthracycline antibiotics (Boucek et al., 1999) and also potentiates the hematotoxicity of DOX (Siveski-Illiskovic et al., 1994). Therefore, there is great need to develop novel interventions which can prevent the cardiotoxic effects of doxorubicin without side effects.

Sildenafil citrate (Viagra) is a potent selective inhibitor of phosphodiesterase-5 (PDE-5) which is known to enhance erectile function in men by allowing an increase in cGMP in vascular smooth muscle cells (Nazeyrollas et al., 1999). In Examples 1 and 2, it was shown that intravenous or oral administration of sildenafil citrate induces a powerful cardioprotective effect against ischemia-reperfusion injury in rabbit hearts. The hypothesis behind the studies was that the vasodilatory action of sildenafil could potentially release endogenous mediators of preconditioning such as adenosine, bradykinin, or nitric oxide (NO). One or more of these mediators may trigger the signaling cascade leading to opening of $MITOK_{ATP}$ channels resulting in acute and delayed cardioprotective effects.

In this study, the prevention of cardiomyocyte apoptosis and subsequent development of cardiomyopathy in a chronic mouse model of doxorubicin-induced cardiotoxicity is demonstrated. Mice are treated with doxorubicin in the presence or absence of clinically relevant doses of sildenafil citrate, and the left ventricular systolic function is correlateed using 2-dimensional (2D) contrast echocardiography. The actions of dosing sildenafil citrate 24 hours prior to each dose of doxorubicin (Total of 3 doses) versus dosing sildenafil citrate daily for 28 days is tested. Histological examination is performed to assess the ultrastructural alterations including nuclear condensation with coarse chromatin clumping, sarcoplasmic reticulum vacuolization, and mitochondrial fine structure disruption which are known to occur widely in doxorubicin-treated cardiomyocytes. The effect of sildenafil in reducing necrotic and apoptotic cell death in the adult mice cardiomyocytes following treatment with DOX is demonstrated. The role of sildenafil in attenuation of DOX-induced apoptosis and attenuation of mitochondrial transition pore opening is assessed. The contribution of $MITOK_{ATP}$ channel opening in rescuing DOX-induced cell death in sildenafil treated mice is determined by using 5-hydroxydecanoate, a selective blocker of the $MITOK_{ATP}$ channel. This study is the first to demonstrate the protective effect of sildenafil in DOX-induced cardiotoxicity in the heart at the cellular and sub-cellular levels.

The ability of sildenafil to inhibit doxorubicin-induced apoptosis by opening of $MITOK_{ATP}$ channel, prevention of the collapse of the mitochondrial membrane potential ($\Psi$m), and attenuation of the mitochondrial transition pore opening, are also tested. The relevance of the $MITOK_{ATP}$ channel in promoting cardioprotection has been well documented (Garlid et al., 1997). Specifically, the opening of $MITOK_{ATP}$ channels is critical in mediating the cardioprotective effect induced by pathophysiological stressors and pharmacological agents. The activation of these channels is triggered by a drop in tissue ATP levels which result in preventing the dissipation of the mitochondrial membrane potential (Ockaili et al., 1999).

The collapse of $\Psi$m is a prominent feature of apoptotic cell death and has been suggested as an irreversible marker of cellular commitment to the apoptotic cell death pathway (Xu et al., 1976). Breakdown of the mitochondrial membrane potential ($\Psi$m) may precede nuclear signs of apoptosis, and it may be associated with $Ca^{2+}$ homeostasis. A recent elegant study from Marban's group has shown that pharmacological opening of $MITOK_{ATP}$ channels by diazoxide preserved mitochondrial integrity, prevented depolarization of the mitochondrial membrane potential and translocation of cytochrome-c to the cytosol following in vitro oxidative stress (Kalyanaraman et al., 2002). Since sildenafil-induced cardioprotection is mediated by opening of $MITOK_{ATP}$ channel via mechanisms similar to diazoxide, sildenafil citrate allows maintenance of the mitochondrial membrane potential ($\Psi$m) and reduction of cytochrome c release from the mitochondria leading to inhibition of apoptosis in DOX-treated myocytes.

Materials and methods. Adult male mice (~30 g each) are randomized to one of four groups. Experimental animals are treated using either DOX. (5 mg/kg) or an equivolume of saline ip on days 1, 14, and 21, representing a total cumulative dose of 15 mg/kg. Sildenafil citrate (0.7 mg/kg, ip equivalent to 50 mg of an oral dose used clinically by patients for erectile dysfunction) is administered 24 hours before each dose of DOX for a total of three doses and a second group receives sildenafil citrate from days 0–28. The animals are sacrificed ten weeks after the last DOX treatment or after a total of 14 weeks from beginning of study, whichever endpoint is reached first. Weight of all animals is measured weekly and gross heart weight is measured prior to freezing in liquid nitrogen. Immediately following animal sacrifice and just prior to freezing, biopsies are taken from the left ventricles and placed in 2% glutaraldehyde for subsequent immunogold TUNEL staining utilizing electron microscopy. Specifically, nuclear chromatinmargination, mitochondrial swelling, cristae disappearance/matrix clearing, presence or absence of contractile apparatus disarray, and sarcoplasmic reticulum vacuolization is measured. Left ventricular function is evaluated by 2-D contrast echocardiography as demonstrated previously (Doroshow et al., 1980).

The protective effect of sildenafil against DOX-induced cardiotoxicity at the cellular level is also investigated. Neonatal mouse myocytes in culture are incubated with 0.5–5 $\mu$M of DOX (in the presence or absence of 1 $\mu$M sildenafil) for 18 hours. The cells are then incubated with drug free growth medium for an additional 24 hours. Cytotoxicity of DOX is quantitatively assessed by measuring the percentage of cells killed and the amount of creatine kinase (CK) released into the media. In addition, a trypan blue exclusion assay and propidium iodide nuclear stain are used to quantitate cell death. Since DOX induces cardiomyopathy through the release of reactive oxygen species, lipid peroxidation in the cells is also measured as an index of oxidative damage.

Neonatal mouse cardiac myocyte cultures are used for membrane potential studies. Cells in culture are treated with 0.5–5 $\mu$M of DOX (in the presence or absence of 1 $\mu$M sildenafil) for 18 hours. The cells are then incubated with drug free growth medium for an additional 24 hours. Additional groups are included where the cells are treated with a $mitoK_{ATP}$ channel blocker (5-hydroxydecanoate, 100 $\mu$M), surface channel blocker (HMR1098, 30 $\mu$M) or cyclosporine, a mitochondrial membrane potential ($\Psi$m) blocker (5 $\mu$M). For assessment of apoptosis, the TUNEL assay is used, which is an accurate method for distinguishing apoptosis from necrosis by specifically detecting DNA cleavage and chromatin condensation characteristic of apoptosis. Additionally, positive TUNEL staining directly correlates with the more typical biochemical and morphological aspects of apoptosis. Since an understanding of cell morphology is critical for data interpretation, apoptotic morphology is simultaneously assessed according to accepted scientific criteria previously described (Nor-Avi, 1999). The in situ staining of DNA strand breaks detected by the TUNEL assay along with subsequent morphological observation via epifluorescent, confocal, and electron microscopy, provides significant and reliable data regarding the identification of apoptotic cells, even in tissue samples where apoptosis represents a small segment of the population (Manning 1994). In addition, several other key indicators of apoptosis including annexin-V, cytosolic cytochrome c, caspase 3, caspase 8, as well as poly (ADP-ribose) polymerase cleavage in these groups, are measured. Mitochondrial membrane potential ($\Psi$m) using a fluorescent indicator probe, JC-1 (Molecular Probes, Eugene, Oreg.) is measured.

Results

The results show the following:
1) Sildenafil reduces ultrastructural damage to the heart and improves LV function in DOX-treated mice when compared to control animals;
2) Cells exposed to DOX demonstrate increased necrotic cell death as indicated by increased CK release and uptake of trypan blue. In addition, enhanced lipid hydroperoxides are observed. However, these parameters of injury are reversed in cells treated with sildenafil;
3) DOX treated myocytes demonstrate TUNEL positivity, translocation of cytochrome c to the cytosol, caspase-3 activation, poly(ADP-ribose) polymerase cleavage, and dissipation of the mitochondrial membrane potential ($\Psi$m). These deleterious effects are aborted in the groups where the cells are treated with DOX in the presence of sildenafil. In addition, the protective effect of sildenafil is abolished by 5-hydroxydecanoate but not by HMR1098.

Example 5

Vardenafil (Lavitra) Induces Cardioprotective Effect in Rabbits

Vardenafil (Bayer) is a fairly new impotence drug which acts a Phosphodiesterase-5 (PDE-5) inhibitor and that is used to treat male erectile dysfunction. Rabbits were treated with Vardenafil (5 mg/kg, iv) for 30 minutes, hearts were subjected to 30 minutes of ischemia by occlusion of the coronary artery and reperfusion for 180 minutes, as described in Example 1 for sildenafil. Control rabbits were treated with an equivalent volume of saline. The results are presented in FIG. 4, which shows a significant reduction of myocardial infarct size (% of risk area) in the Vardenafil-treated rabbits as compared to the controls. This study further supports the concept that PDE-5 inhibitors induce cardioprotective effects in mammals.

Example 6

Sildenafil Citrate Induces Cardioprotection in Infant Rabbits

Surgery for congenital heart disease often employs cardiopumonary bypass, circulatory arrest with deep hypothermia or low flow states. Infant myocardium is particularly more vulnerable to ischemic injury than the adult myocardium. The cardioprotective effect of sildenafil was tested in infant rabbits. The infant rabbits (aged 8 weeks) were treated with sildenafil (0.7 mg/kg) or normal saline (control) 30 minutes prior to ischemia which was induced by ligation of the coronary artery. The hearts were then reperfused for 3 hrs. Infarct size was determined by TTC staining. The results are given in FIG. 5. As can be seen, the Sildenafil-treated group demonstrated significant reduction in infarct size from 33±1.5 to 16.8±1.0 (% risk area, mean±SEM). These results prove the efficacy of sildenafil in protecting ischemic injury in infant rabbits.

Example 7

Sildenafil Induces Delayed Preconditioning Through iNOS-Dependent Pathway in Mouse Heart Sildenafil citrate (Viagra) is a selective inhibitor of phosphodiesterase-5, which catalyzes the breakdown of cGMP, one of the primary factors involved in smooth muscle relaxation. It enhances NO-driven cGMP accumulation, which, in turn, causes vasodilatation in the corpus cavernosum. Sildenafil has become the most widely used drug for treating erectile dysfunction in men since its market debut in 1998 (Boolell et al., 1996). Interestingly, we recently discovered a powerful preconditioning-like effect of sildenafil in rabbit hearts (Ockaili et al, 2002). Both intravenous and oral administration of sildenafil caused significant reduction of infarct size after ischemia-reperfusion (I-R). The protection was abolished by 5-hydroxydecanoate, a selective blocker of mitochondrial ATP-dependent K+(mitoK$_{ATP}$) channels (Ockaili et al, 2002). However, the mechanism by which sildenafil triggers the signaling cascade leading to the opening of mitoK$_{ATP}$ remains speculative. There is mounting evidence suggesting a role of NO in modulating mitoK$_{ATP}$. (Ockaili et al, 1999; Sasaki et al., 2000; Gross, 2000; Wang et al., 2001). The synthesis of NO is catalyzed by 3 isoforms of NO synthase (NOS), namely, neuronal NOS, inducible NOS (iNOS), and endothelial NOS (eNOS), among which iNOS has been identified as the essential mediator of delayed preconditioning induced by divergent pathophysiological stimuli or pharmacological agents, such as brief episodes of I-R (Guo et al., 1999), endotoxin derivatives (Zhao et al., 1997; Xi et al. 1999) G-protein-coupled membrane receptor agonists (Zhao et all, 2000; Tejero-taldo et al., 2002), whole-body hyperthermia (Armaud et al, 2001), and systemic hypoxia (Xi et al, 2002). However, no studies are available showing any link between sildenafil and the activation of a NOS dependent signaling cascade. The goal of the present report was to determine whether (1) sildenafil induces the synthesis of NOS isoforms in the heart and (2) iNOS mediates the delayed preconditioning effect in the mouse heart.

MATERIALS AND METHODS

Physiological Studies

Adult male outbred ICR mice were supplied by Harlan Inc (Indianapolis, Ind.). Viagra pills (Pfizer Inc) were ground into powder and dissolved in saline. The drug solution was filtered (0.45-μm pore size) before intraperitoneal injection. 1400W, an iNOS inhibitor, was obtained from Alexis. We used an isolated perfused mouse heart model subjected to 20 minutes of global ischemia and 30 minutes of reperfusion (Langendorff mode). Myocardial I-R injury was assessed by measuring infarct size, contractile function, and coronary flow as described previously (Xi, 1999). Twenty-eight mice were randomized into the following 4 groups: (n=6 to 9 per group): (1) saline (0.15 mL IP), (2) sildenafil (0.7 mg/kg IP, equivalent to 50 mg Viagra pill used for patients with erectile dysfunction, given 24 hours before I-R), (3) sildenafil+1400W (10 mg/kg IP, 14 given 30 minutes before I-R), and (4) saline+1400W.

Measurement of NOS Isoforms

Mice were treated with sildenafil (0.7 mg/kg IP), and their hearts were removed at 15, 30, and 45 minutes and 1, 2, 3, 4, and 24 hours after injection (n=3 per group). Three nontreated hearts were used as controls. Tissue samples were ground under liquid nitrogen and homogenized with TRI Reagent (Molecular Research Center) for extracting total RNA, which was reverse-transcribed into cDNA at 50° C. for 30 minutes using a OneStep reverse transcription (RT)-polymerase chain reaction (PCR) kit from Qiagen. The oligonucleotide primers were synthesized on the basis of published sequences for murine iNOS, eNOS, and GAPDH15 (Integrated DNA Technology). The RT-PCR products were electrophoresed on 1.5% Trisacetate-EDTA agarose gel. The target bands were identified on the basis of their specific size using DNA standards. iNOS and eNOS proteins were measured by Western blots as described previously. 13 In brief, triplicate heart samples were collected 24 hours after saline or sildenafil injection and homogenized in ice-cold RIPA buffer (Upstate Biotechnology). The homogenate was centrifuged at 10,000 g for 10 minutes at 4° C., and supernatant was recovered as the total cellular protein. Total protein (60 µg) from each sample was separated by SDS-PAGE on 10% acrylamide gels, transferred to a polyvinylidine difluoride membrane, and then blocked with 5% nonfat dry milk in Tris-buffered saline. The membrane was subsequently incubated with a rabbit polyclonal antibody (dilution 1:500, Santa Cruz) reacting specifically to iNOS, eNOS, or actin. The secondary antibody was a horseradish peroxidase-conjugated anti-rabbit IgG (1:1000 dilution, Amersham). The membranes were developed using enhanced chemiluminescence and exposed to x-ray film. The mRNA and protein expression were quantified by scanning each of the RT-PCR or Western blot band using a densitometer (Bioquant 98).

Data Analysis and Statistics

Data are presented as mean±SEM. The difference among the treatment groups or the time points after sildenafil injection was compared by unpaired t test or 1-way ANOVA, followed by the Student-Newman-Keuls post hoc test. A value of $P<0.05$ was considered significant.

Results and Discussion

Figure 6:
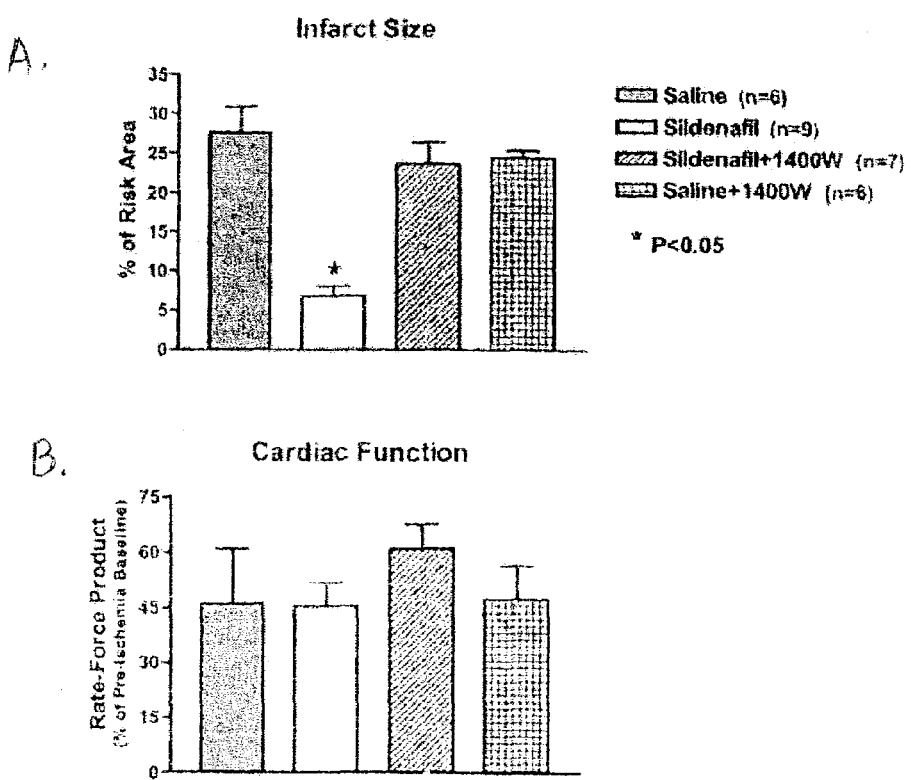

Pretreatment of the mice with sildenafil reduced their infarct sizes 24 hours later (6.9±1.2%) compared with saline (control) treatment (27.6±3.3%, $P<0.05$; FIG. 6A). The infarct limiting effect of sildenafil was not associated with compromised ventricular contractile function, ie, stunning (FIG. 6B), which is in agreement with the results of Przyklenk and Kloner (2001). Sildenafil did not alter preischemic or postischemic coronary flow (data not shown), indicating that its cardioprotective effect may be independent of its vascular response 24 hours later. These results confirmed our previous findings showing a powerful cardioprotective effect of sildenafil in the rabbit heart (Ockaili et al, 2002). There was an increase in iNOS and eNOS mRNA and protein expression (FIGS. 7 and 8). The levels of these transcripts increased transiently, peaking at 45 minutes (eNOS) and 2 hours (iNOS) after sildenafil treatment and returning to baseline levels several hours later (FIG. 7). The magnitude of increase was much higher for iNOS compared with eNOS. In addition, sildenafil-induced protection was abolished by the selective iNOS inhibitor 1400W (infarct size 23.7±2.8%, $P<0.05$ versus sildenafil). 1400W had no significant effect on infarct size compared with the effect of saline (24.5±1.0%, $P>0.05$ versus saline).

Several studies have shown that NO derived from iNOS plays a major role in the delayed cardioprotection induced by endotoxin derivatives (Zhao et al., 1997; Xi et al, 1999) agonists of adenosine or adrenergic receptors (Zhao et al., 2000; Tejero-Taldo, 2002) p38 activator (Zhao et al., 2001) and diazoxide, a mitoKATP opener (Wang et al, 2001). The role of sildenafil in stimulating the release of NO in the heart is unknown. We provide the first evidence indicating that sildenafil is a potent inducer of iNOS mRNA and protein, which lead to delayed cardioprotection. Although eNOS mRNA and protein also increased, their quantitative expression was lower than that of iNOS. The role of eNOS is not clear in the present study. The complete blockade of cardioprotection with 1400W given before ischemia rules out the role of eNOS in the mediator phase of delayed protection. However, eNOS may play a role in the trigger phase, ie, at the time of sildenafil treatment when NO from eNOS may initiate the signaling cascade leading to iNOS expression, as proposed by Bolli (Bolli, 2000; Bolli, 2001). The iNOScatalyzed NO generation could potentially activate guanylate cyclase, resulting in an enhanced formation of cGMP. cGMP may activate protein kinase G, which can subsequently open mitoKATP channels, resulting in the cardioprotective effects as recently reported (Han et al., 2002)

In conclusion, our results show, for the first time, that sildenafil induces delayed preconditioning, which is primarily mediated by NO derived from iNOS. The present study in a model of global I-R further expands our knowledge regarding the cardioprotective effect of sildenafil, which may potentially be used in the treatment of patients with ischemic heart diseases.

Example 8

The Effects of Sildenafil Protection in Genetically Engineered Gene-Knockout Mice Methods Animals: Adult male iNOS gene-knockout (−/−) B6,129 mice are purchased from the Jackson Laboratory (Bar Harbor, Me.). Chimeric mice were generated by injecting C57BL/6J (B6) blastocysts with recombinant 129-derived embryonic stem cells and implanted into pseudopregnant females for development. Chimeric males were then mated with B6 females, and the resulting B6,129 F1 heterozygous mutant mice (+/−) were interbred to generate F2 homozygous mutant (−/−) mice for the disruption of NOS 1, 2, or 3. Their progeny is genotyped by Southern analysis. On their arrival, the animals are allowed to readjust to the new housing environment for 3 days before any experiment. Standard rodent food and water will be freely accessible. All animal experiments are conducted under the guidelines on humane use and care of laboratory animals for biomedical research published by the National Institutes of Health (publication No. 85-23, revised 1996).

Drugs and Chemicals

L-NAME (L-nitro-L-arginine methyl ester), L-NIL(L-N-6-(1-iminoethyl)lysine hydrochloride)), SMT (S-methyl-L-thiocitrulline), 1400W and triphenyltetrazolium chloride (TTC) are purchased from Sigma Chemical Co. The primary antibodies are purchased from Santa Cruz Biotechnology Inc, and anti-rabbit Ig horseradish peroxidase-linked whole antibody is purchased from Amersham.

Langendorff's Isolated Perfused Heart Preparation

The methodology of the Langendorff-perfused mouse heart preparation was described elsewhere in several publications (Tajero-Taldo et al., 2003; Xi et al., 1999; Xi et al., 2000; Xi and Kukreja, 1999; Zhao and Kukreja, 2001a; Zhao and Kukreja, 2002; Zhao and Kukreja, 2001b; Zhao et al., 2000; Fujii et al., 1997). In brief, the animal is anesthetized with sodium pentobarbital (120 mg/kg, 33 U heparin, i.p.) and heart is quickly removed from the thorax, placed into a small dish containing ice-cold perfusate with heparin. The aortic opening of the heart is rapidly cannulated and tied on a 20 gauge blunt needle that is in turn connected to a Langendorff perfusion system. Following cannulation, heart is retrogradely perfused at a constant pressure of 55 mmHg with modified Krebs-Henseleit solution which contains (in mM): NaCl 118, NaHCO$_3$ 24, CaCl$_2$ 2.5, KCl 4.7, KH$_2$PO$_4$ 1.2, MgSO$_4$ 1.2, Glucose 11EDTA 0.5. The perfusion solution is continuously gassed with 95% O$_2$+5% CO$_2$ (pH 7.34–7.49) and warmed by a heating/cooling bath. The heart temperature is continuously monitored and maintained at 37° C. throughout the experiment.

A left atrial incision is made to expose the mitral annulus, through which a water-filled latex balloon is passed into the left ventricle as described previously (Knowles and Moncada, 1994). The balloon is attached via polyethylene tubing to a Gould pressure transducer that is connected to a Power Lab Myocardial Function Recorder. The balloon is inflated to adjust the left ventricular end-diastolic pressure (LVEDP) to 10 mm Hg. Myocardial injury is measured with multiple, independent end points of tissue injury. These include infarct size, left ventricular developed pressure (LVDP), LVEPD, rate-pressure product (RPP), heart rate, and coronary flow. Heart rate, LVDP, LVEDP, and maximum positive or negative first derivative of left ventricular pressure ($\pm dP/dT_{max}$) (the index of inotropic state) is monitored and recorded continuously. LVDP will be calculated by subtracting LVEDP from the peak systolic pressure. RPP, an index of cardiac work is calculated by multiplying LVDP by heart rate.

Measurement of Risk Area and Infarct Size: Following completion of the protocol, the heart is frozen for 24 hours. The frozen heart is cut into eight transverse slices of equal thickness (approximately 0.8 mm) from the apex to the base. Hearts are sectioned into transverse slices. These slices are then be incubated in a 10% tirphenyltetrazolium (TTC) solution in an isotonic buffer (pH 7.4) at 37° C. for 30 minutes. TTC reacts with NADH present only in viable tissue producing a deep red stain allowing this to be distinguished from the non-staining infarcted myocardium. Total ventricular area, cavity area, and infarct area is determined by computer morphology using digital planimetry with Bioquant 98 software. The risk area corresponds to the sum of the total ventricular area minus cavities. The infarct size is calculated and presented as a percentage of the total risk area.

Western Blot Analysis

Hearts are weighed and homogenized with 6 bursts of 15 seconds each at 4° C. with a Polytron PT 20 in 1 ml RIPA buffer (1×PBS, 1% Nonidate P-40, 0.5% sodium deoxycholate, 0.1% SDS, 10 mmol/L PMSF, 30 mL/ml aprotinin, and 100 mmol/L sodium orthovanadate). Subsequently, the samples are centrifuged at 14,000 rpm for 10 minutes. The pellet is discarded, and the protein in the supernatant is determined. Standard SDS gel electrophoresis is performed with 20 µg of protein loaded in each well of a 12% polyacrylamide gel. After electrophoresis, the protein is transferred to a nitrocellulose membrane for 2 hours at 100 V. The membrane is blocked with 5% no-fat dry milk in 1Xtris-buffered saline containing 0.1% Tween 20 (TMST 0.1%) for 1 hour. The membrane is incubated with the primary antibody (dilution 1:1000) for 1 hour at room temperature. After washing with TBST 0.1%, the membrane is incubated with anti-rabbit horseradish peroxidase-linked antibody (dilution 1:500) for 1 hour. The membranes are developed with enhanced chemiluminescence (Amersham) and exposed to x-ray film for the appropriate amount of time.

NO Measurements: Hearts (n=4–5 per group) from mice are collected, powdered under liquid nitrogen, and homogenized at 4° C. with a Polytron PT 20 (4 bursts of 5 seconds each) in 5 volumes of PBS, pH 7.4, then centrifuged at 14,000 rpm for 10 minutes and the pellets discarded. Samples are de-proteinized with 200° proof ethyl alcohol at 0° C. in a 1:2 v/v mix, incubated 30 minutes at 0° C. and then centrifuged at 14,000 rpm for 5 minutes, discarding the pellets. Inactivated NO in the form of nitrate, nitrite and S-nitrosocompounds (NO$_x$) is reduced to NO with vanadium (III)—HCl. Tissue NO will be measured based on a gas-phase chemiluminescent reaction between NO and ozone with a NOA 280™ (Sievers Instruments, Boulder, Colo.).

RT-PCR of nNOS/iNOS/eNOS

Total cellular RNA is isolated from LV tissue with Trizol reagent (Gibco BRL, Life Technologies). RNA (5 µg) is reverse transcribed to generate cDNA using standard methodology. The reverse-transcribed cDNA (10 µL) is amplified in a final volume of 100 µL by PCR under standard conditions (1.5 mmol/L MgCl$_2$, 200 µmol/L dNTP, 4.0 U Taq polymerase) with 50 µmol/L of primers for iNOS based on the sequence for murine iNOS cDNA. The primers for nNOS, iNOS or eNOS will be synthesized. The proposed experimental conditions for PCR are: 30 cycles for 60 s at 94° C., 55° C. and 72° C. After amplification, 10 µl of PCR product per lane is resolved on 1.5% agarose gel containing ethidium bromide in 1×TBA buffer. Bands are confirmed under UV fluorescence and purified by using a Qiagen purification kit. The nucleotide sequences for iNOS is determined by the same up primer used for PCR reaction and a DNA sequencer.

The effects of sildenafil in protection in genetically engineered gene-knockout mice for three isoforms of the NOS i.e., neuronal (nNOS), inducible (iNOS) and endothelial constitutive (eNOS), in which one of the NOS genes has been deleted, is investigated. It is important to employ the two experimental strategies (pharmacologic inhibition and targeted gene deletion) due to the following reasons: While SMT, 1400W and L-NIL are widely regarded as selective iNOS inhibitors, the selectivity of these agents for iNOS vs nNOS is relative (approximately 40 fold). The targeted gene deletion approach firmly establishes a role of NNOS, iNOS, or eNOS in sildenafil-induced delayed cardioprotection.

The wild-type (WT) and each of the knockout (KO) mice (nNOS, iNOS, and eNOS) are treated with sildenafil. The animals are allowed to recover for 24 hrs. For ischemia/reperfusion studies, the hearts are isolated and subjected to 30 min of global ischemia and 60 min of reperfusion. The following groups are studied: 1) WT-saline treated, 2) WT-sildenafil treated, 3) nNOS-KO+sildenafil, 4) iNOS-KO+sildenafil and 5) eNOS-KO+sildenafil. Group 6–8 hearts will serve as saline-treated controls for nNOS, iNOS and eNOS respectively. A total of 64 mice (8 animals/group) are used for these studies. Assessed parameters are (a) Infarct Size. (b) Myocardial function (LVDP, LVEDP, CF, heart rate and CK release).

The studies provide conclusive evidence for the role of NOS isoform(s) responsible for delayed cardioprotection. The delayed cardioprotection induced by sildenafil is absent in the iNOS-KO mice but not in nNOS or eNOS-KO mice.

Example 9

Cardioprotective Effect of Sildenafil at Lower Doses

In order to further determine the cardioprotective effect of sildenafil at lower doses, we treated rabbits with 0.2 mg/kg (equivalent to 14 mg dose a 70 kg patient, n=3 per group) and 0.1 mg/kg (equivalent to 7.1 mg dose for a 70 kg patient) 30 minutes prior to a 30 minutes of regional ischemia and 3 hrs of reperfusion. Myocardial infarct size was measured at the end of reperfusion. The controls (n=6) were treated with saline only. The results showed dramatic reduction of infarct size from 33.8±0.9 in saline controls to 13.53±1.24 with 0.2 mg/kg sildenafil and 17.05% with 0.1 mg/kg sildenafil. The infarct limiting effect of sildenafil at these lower doses was comparable with the 0.7 mg/kg dose of sildenafil (equivalent to 50 mg for treatment of MED for a 70 kg patient) as shown in FIG. 2A. These data strongly suggest sildenafil as well as other PDE-5 inhibitors may be effective in reducing ischemia/reperfusion injury at much lower doses than those necessary for treatment of MED.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Allen A. The cardiotoxicity of chemotherapeutic drugs. *Semin Oncol* 1992; 19: 529–542.

American Heart Association. Heart Disease and Stroke Statistics—2003 Update. Dallas, Tex.: American Heart Association; 2002.

Auchampach, J. A. and G. J. Gross. Adenosine A1 receptors, $K_{ATP}$ channels, and ischemic preconditioning in dogs. *Am J Physiol* 33: H1327–H1336, 1993.

Baxter, G. F. and D. M. Yellon. ATP-sensitive K+ channels mediate the delayed cardioprotective effect of adenosine A1 receptor activation. *J Mol Cell Cardiol* 31: 981–989, 1999.

Bernardo, N. L., Okubo, S, Maaieh, M., Wood, M and Kukreja, R. C. Delayed preconditioning with adenosine is mediated by opening of ATP-sensitive K+ channel in rabbit heart. *Am J Physiol.* 1999 277: H128–H135, 1999a.

Bernardo, N. L., D'Angelo, M., Okubo, S and Kukreja, R. C. (b) ATP-sensitive potassium channel is involved in the second window of preconditoning. *Am J Physiol,* 276: H1323–30, 1999b.

Bolli, R., S. Manchikalapudi, X. L. Tang, H. Takano, Y. Qiu, Y. Guo, Q. Zhang, and A. K. Jadoon. The protective effect of late preconditioning against myocardial stunning in conscious rabbits is mediated by nitric oxide synthase. Evidence that nitric oxide acts both as a trigger and as a mediator of the late phase of ischemic preconditioning. *Circ Res* 81: 1094–1097, 1997.

Bolli, R. The late phase of preconditioning. Circ Res 87: 972–983, 2000.

Bolli R. Cardioprotective function of inducible nitric oxide synthase and role of nitric oxide in myocardial ischemia and preconditioning: an overview of a decade of research. *J Mol Cell Cardiol.* 2001;33: 1897–1918.

Boolell M, Allen M J, Ballard S A, Gepi-Attee S, Muirhead G J, Naylor A M, Osterloh I H, Gingell C. Sildenafil: an orally active type 5 cyclic GMP-specific phosphodiesterase inhibitor for the treatment of penile erectile dysfunction. *Int J Impot Res.* 1996;8:47–52.

Boucek R J, Jr., Miracle A, Anderson M, et al. Persistent effects of doxorubicin on cardiac gene expression. *J Mol Cell Cardiol* 1999; 31(8):1435–46.

Cheitlin, M. D., A. M. Hutter, R. G. Brindis, and et al. Use of sildenafil (Viagra) in patients with cardiovascular disease. *J Am Coll Cardiol* 33: 273–282, 1999.

Cohen, M. V., C. P. Baines, and J. M. Downey. Ischemic preconditioning: from adenosine receptor to $K_{ATP}$ channel. *Annu. Rev. Physiol* 62: 79–109, 2000.

Corbin, J. D., S. H. Francis, and D. J. Web. Phosphodiesterase type 5 as a pharmacologic target in erectile dysfunction. *Urology* 60 (2): 4–11, 2002.

Doroshow J H, Locker G Y, Myers C E. Enzymatic defenses of the mouse heart against reactive oxygen metabolites: alterations produced by doxorubicin. *J Clin Invest* 1980; 65(1):128–35.

Ferrans V. Overview of cardiac pathology in relation to anthracycline cardiotoxicity. Cancer Treat Rep 1978; 62:965–1.

Fryer, R. M., A. K. Hsu, J. T. Eells, H. Nagase, and G. J. Gross. Opoid-induced second window of cardioprotection: potential role of mitochondrial $K_{ATP}$ channels. *Circ Res* 99: 846–851, 1999.

Fujii, M., H. Hara, W. Meng, J. P. Vonsattel, Z. Huang, and M. A. Moskowitz. Strain-related differences in susceptibility to transient forebrain ischemia in SV-129 and C57black/6 mice. *Stroke* 28: 1805–1810, 1997.

Garlid K, Paucek, P, Yarov-Yarovoy, V, Murray, H N, Darbenzio, R B, D'Alonzo, A J, Lodge, N J, Smith, M A, Grover, G J. Cardioprotective effect of diazoxide and its interaction with mitochondrial ATP-sensitive K+ channels: possible mechanism of cardioprotection. *Circ Res* 1997;81:1072–1082

Gross, S. S. and M. S. Wolin. Nitric oxide: pathophysiological mechanisms. *Ann Rev Physiol* 57: 737–769, 1995.

Gross G J. The role of mitochondrial KATP channels in cardioprotection. *Basic Res Cardiol.* 2000;95:280–284.

Gross, G. J. and R. M. Fryer. Sarcolemmal versus mitochondrial ATP-sensitive K+ channels and myocardial preconditioning. *Circ Res* 84: 973–979, 2001.

Guo, Y., W. K. Jones, Y. T. Xuan, X. L. Tang, W. Bao, W. J. Wu, H. Han, V. E. Laubach, P. Ping, Z. Yang, Y. Qiu, and R. Bolli. The late phase of ischemic preconditioning is abrogated by targeted disruption of the inducible NO synthase gene. *Proc Natl Acad Sci USA* 96: 11507–11512, 1999.

Han J, Kim N, Joo H, Kim E, Earm YE. ATP-sensitive K+ channel activation by nitric oxide and protein kinase G in rabbit ventricular myocytes. *Am J Physiol.* 2002;283: H1545–H1554.

Han, J., N. Kim, E. Kim, W. K. Ho, and Y. E. Earm. Modulation of ATP-sensitive potassium channels by cGMP-dependent protein kinase in rabbit ventricular myocytes. *J Biol. Chem* 276: 22140–22147, 2001.

Ide T, Tsutsui, H, Kinugawa, S, Suematsu, N, Hayashidani, S, Ichikawa, K, Utsumi, H, Machida, Y, Egashira, K, Takeshita, A. Direct evidence for increased hydroxyl radicals originating from Superoxide in the failing myocardium. *Circ Res* 2000;86:152–157.

Janin, Y., Y.-Z. Qian, J. B. Hoag, G. T. Elliott, and R. C. Kukreja. Pharmacologic preconditioning with monophosphoryl lipid A isabolished by 5-hydroxydecanoate, a specific inhibitor of the $K_{ATP}$ channel. *Cardiovasc Pharmacol* 32: 337–342, 1998.

Kalyanaraman B, Joseph J, Kalivendi S, et al. Doxorubicin-induced apoptosis: implications in cardiotoxicity. *Mol Cell Biochem* 2002;234–235(1–2):1 19–124.

Keizer H, Pinedo, H M, Schuurhuis, G J, and Joenje, H. Doxorubicin (Adriamycin): a critical review of free radical-dependent mechanism of cytotoxicity. *Pharmacol Ther* 1990;47:219–231.

Kloner, R. A. and J. P. Jarow. Erectile dysfunction and sildenafil citrate and the cardiologist. *Am J Cardiol* 83: 576–582,1999.

Kloner, R. A. Cardiovascular risk and sildenafil. *Am J Cardiol* 86: 57–61, 2000.

Kloner, R. A. and R. M. Zusman. Cardiovascular effects of sildenafil citrate and recommendations for its use. *Am J Cardiol* 84: 11–17, 1999.

Koning, J, Palmer P, Franks C R, Mulder D E, Speyer J L, Green M D, and Hellmann K. Cardioxane-IcRF-187 towards anticancer drug specificity through selective toxicity reduction. *Cancer Treat Rev* 1991;18: 1–19.

Knowles, R. G. and S. Moncada. Nitric oxide synthases in mammals. *BIOCHEM J* 298: 249–258, 1994.

Kositprapa, C., R. Ockaili, and R. C. Kukreja. Bradykinin $B_2$ receptor is involved in the late phase of preconditioning in rabbit heart. *J Mol Cell Cardiol* 33: 1355–1362, 2001.

Kumar D, Kirshenbaum L A, Li T, et al. Apoptosis in adriamycin cardiomyopathy and its modulation by probucol. *Antioxid Redox Signal* 2001; 3(1): 135–145.

Liu, Y., N. Sato, B. O'Rourke, and E. Marban. Mitochondrial ATP-dependent potassium channels: novel effectors of cardioprotection *Circulation* 97: 2463–2469, 1998.

Manning, W J. In vivo assessment of LV mass in mice using high frequency cardiac ultrasound: necropsy validation. AM J Physiol, 1994;266 (4Pt 2): H1672–H1675

Mettler F P, Young D M, Ward J M. Adriamycin-induced cardiotoxicity (cardiomyopathy and congestive heart failure) in rats. *Cancer Res* 1977; 37(8 Pt 1):2705–2713.

Murry, C. E., R. B. Jennings, and K. A. Reimer. Preconditioning with ischemia: a delay of lethal cell injury in ischemic myocardium. *Circulation* 74: 1124–1136, 1986.

Nazeyrollas P, Prevost A, Baccard N, et al. Effects of amifostine on perfused isolated rat heart and on acute doxorubicin-induced cardiotoxicity. *Cancer Chemother Pharmacol* 1999; 43(3):227–232

Nor-Avi V, Kocarz, C, Fentzke, R C, Lin, H, Leiden, J M, Lang, R M. Quantitative evaluation of left ventricular function in a transgenic mouse model of dilated cardiomyopathy with 2-dimensional contrast electrocardiography. *Am Soc Echocardio* 1999;12:209–214.

Ockaili R, Emani V R, Okubo S, Brown M, Krottapalli K, Kukreja R C. Opening of mitochondrial $K_{ATP}$ channel induces early and delayed cardioprotective effects: role of nitric oxide. *Am J Physiol.* 1999;277: H2425–H2434.

Ockaili R, Salloum F, Hawkins J, Kukreja R C. Sildenafil (Viagra) induces powerful cardioprotective effect via opening of mitochondrial $K_{ATP}$ channels in rabbits. *Am J Physiol.* 2002;283:H1263–H1269.

Przyklenk, K. and R. A. Kloner. Sildenafil citrate (Viagra) does not exacerbate myocardial ischemia in canine models of coronary artery stenosis. *J Am Coll Cardiol* 37: 286–292, 2001.

Rotella, D. P. Phosphodiesterase 5 inhibitors: current status and potential applications. *Nature Reviews Drug Discovery* 1: 674–682, 2002.

Sasaki N, Sato T, Ohler A, O'Rourke B, Marban E. Activation of mitochondrial ATP-dependent potassium channels by nitric oxide. *Circulation.* 2000;101:439–445.

Singal P K, Iliskovic N. Doxorubicin-induced cardiomyopathy. *N Engl J Med* 1998; 339(13):900–905.

Siveski-Iliskovic, N, Kaul N, and Singal P K. Probucol promotes endogenous antioxidants and provides protection against adriamycin-induced cardiomyopathy in rats. *Circulation,* 1994;89: 2829–2835.

Steinherz L J, Steinherz P G, Tan C T, et al. Cardiac toxicity 4 to 20 years after completing anthracycline therapy. *Jama* 1991; 266(12):1672–1677.

Szewczyk, A. The ATP-regulated K+ channel in mitochondria: five years after its discovery. *Acta Biochim Pol* 43: 713–719, 1996.

Takano, H., R. Bolli, R. G. Black, E. Kodani, X. L. Tang, Z. Yang, S. Bhattacharya, and J. A. Auchampach. $A_1$ or $A_3$ adenosine receptors induce late preconditioning against infarction in conscious rabbits by different mechanisms. *Circ Res* 88: 520–528, 2001.

Takashi, E., Y. Wang, and M. Ashraf. Activation of mitochondrial $K_{ATP}$ channel elicits late preconditioning against myocardial infarction via protein kinase C signaling pathway. *Circ Res* 85: 1146–1153, 1999.

Tejero-Taldo, M. I., E. Gursoy, T. C. Zhao, and R. C. Kukreja. Alpha-adrenergic receptor stimulation produces late preconditioning through inducible nitric oxide synthase in mouse heart. *J Mol Cell Cardiol* 34: 185–195, 2002.

Vinten-Johansen J, Zhao Z Q, Corvera J S, Morris C D, Budde J M, Thourani V H, Guyton R A. Adenosine in myocardial protection in on-pump and off-pump cardiac surgery. Ann Thorac Surg 2003 February;75(2):S691–9 von Harsdorf R, Li, P F, Dietz, R. Signaling pathways in reactive oxygen species-induced cardiomyocyte apoptosis. *Circulation* 1999;99:2934–2941.

Wallis, R. M. The pharmacology of sildenafil, a novel and selective inhibitor of phosphodiesterase (PDE) type 5. *Nippon Yakurigaku Zasshi* 114 (Suppl): 22–26, 1999.

Wallis, R. M., J. D. Corbin, S. H. Francis, and P. Ellis. Tissue distribution of phosphodiesterase families and the effects of sildenafil on tissue cyclic nucleotides, platelet function, and the contractile responses of trabeculae carneae and aortic rings in vitro. *Am J Cardiol* 83 (Suppl): 3–12, 1999.

Wang, Y., M. Kudo, M. Xu, A. Ayub, and M. Asharf. Mitochondrial $K_{ATP}$ channel as an end effector of cardioprotection during late preconditioning: triggering role of nitric oxide. *J Mol Cell Cardiol* 33: 2037–2046, 2001.

Xi L, Jarrett N C, Hess M L, Kukreja R C. Essential role of inducible nitric oxide synthase in monophosphoryl lipid A-induced late cardioprotection: evidence from pharmacological inhibition and gene knockout mice. *Circulation.* 1999;99:2157–2163.

Xi, L., F. Salloum, D. Tekin, N. C. Jarrett, and R. C. Kukreja. Glycolipid RC-552 induces delayed preconditioning-like effect via iNOS-dependent pathway in mice. *Am J Physiol* 277: H2418–H2424, 1999.

Xi L, Tekin D, Gursoy E, Salloum F, Levasseur J E, Kukreja R C. Evidence that NOS2 acts as a trigger and mediator of late preconditioning induced by acute systemic hypoxia. *Am J Physiol.* 2002;283:H5–H12.

Xi, L. and R. C. Kukreja. Pivotal role of nitric oxide in delayed pharmacological preconditioning against myocardial infarction. *Toxicology* 155: 37–44, 2000.

Xu M, Wang Y, Ayub A, Ashraf M. Mitochondrial K(ATP) channel activation reduces anoxic injury by restoring mitochondrial membrane potential Am J Physiol Heart Circ Physiol, 2001:H1295–H1303.41 Lenaz L and Page J. Cardiotoxicity of adriamycin and related anthracyclines. *Cancer Treat Rev* 1976;3:111–120.

Yao, Z., J. A. Auchampach, G. M. Pieper, and G. J. Gross. Cardioprotective effects of monophosphoryl lipid A, a novel endotoxin analogue, in the dog. *Cardiovasc Res.* 27: 832–838, 1993.

Yoshida, K. I., M. M. Maaieh, J. B. Shipley, M. Doloresco, N. L. Bernardo, Y. Z. Qian, G. T. Elliott, and R. C. Kukreja. Monophosphoryl lipid A induces pharmacologic 'preconditioning' in rabbit hearts without concomitant expression of 70-kDa heat shock protein. *Mol. Cell Biochem.* 156: 1–8, 1996.

Ytrehus, K., Y. Liu, and J. M. Downey. Preconditioning protects the ischemic rabbit heart by protein kinase C activation. *Am J Physiol* 266: H1145–H1152, 1994.

Zhang J, Clark J R, Jr., Herman E H, Ferrans V J. Doxorubicin-induced apoptosis in spontaneously hypertensive rats: differential effects in heart, kidney and intestine, and inhibition by ICRF-187. *J Mol Cell Cardiol* 1996; 28(9): 1931–1943.

Zhao, T., L. Xi, J. Chelliah, J. E. Levasseur, and R. C. Kukreja. Inducible nitric oxide synthase mediates delayed myocardial protection induced by activation of adenosine $A_1$ receptors: evidence from gene-knockout mice. *Circulation* 102: 902–907, 2000.

Zhao L, Weber P A, Smith J R, Comerford M L, Elliott G T. Role of inducible nitric oxide synthase in pharmacological "preconditioning" with monophosphoryl lipid A. *J Mol Cell Cardiol.* 1997;29:1567–1576.

Zhao, T. C. and R. C. Kukreja. Adenosine-induced late preconditioning in mouse hearts: role of p38 MAP kinase and mitochondrial $K_{ATP}$ channels. *Am J Physiol* 280: H1278–H1285, 2001.

Zhao, T. C. and R. C. Kukreja. p38 Triggers late preconditioning elicited by anisomycin in heart: involvement of NF-kB and iNOS. *Circ Res* 89: 915–922, 2001.

Zhao, T. C. and R. C. Kukreja. Late preconditioning elicited by activation of adenosine $A_3$ receptor in heart: role of NF-k B, iNOS and mitochondrial $K_{ATP}$ channel *J Mol Cell Cardiol* 34: 263–277, 2002.

Zhao, T. C., M. M. Taher, K. C. Valerie, and R. C. Kukreja. p38 triggers late preconditioning elicited by anisomycin in heart: Involvement of NF-kappaB and iNOS. *Circ Res* 189: 915–922, 2001.

I claim:

1. A method of treating myocardial infarction caused by ischemic-reperfusion injury in a patient, comprising the step of administering to said patient in need thereof an effective amount of a composition consisting essentially of a phosphodiesterase-5 (PDE-5) inhibitor selected from the group consisting of sildenafil, vardenafil and tadalafil to reduce infarct size, wherein said effective amount is 5 mg or less.

2. A method of claim 1 wherein said step of administering is performed after said ischemic-reperfusion injury.

3. The method of claim 1 wherein said step of administering is via an intraperitoneal route.

4. The method of claim 1 wherein said step of administering is via an oral route.

5. The method of claim 1 wherein said step of administering is via an intravenous route.

6. The method of claim 1 wherein said step of administering is via an intracoronary route.

7. The method of claim 1 wherein said patient is a human.

8. The method of claim 1 wherein said patient is a non-human mammal.

9. The method of claim 1 wherein 1 mg or less of said PDE-5 inhibitor is administered.

* * * * *